(12) United States Patent
Nakagawara et al.

(10) Patent No.: US 7,238,796 B2
(45) Date of Patent: Jul. 3, 2007

(54) HUMAN BMCC1 GENE

(75) Inventors: Akira Nakagawara, Chiba (JP); Masahira Hattori, Fuchu (JP); Yoshiyuki Sakaki, Yokohama (JP)

(73) Assignee: Hisamitsu Pharmaceutical Co., Inc., Tosu-Shi, Saga (JP)

( * ) Notice: Subject to any disclaimer, the term of this patent is extended or adjusted under 35 U.S.C. 154(b) by 210 days.

(21) Appl. No.: 10/487,593

(22) PCT Filed: Aug. 23, 2002

(86) PCT No.: PCT/JP02/08520

§ 371 (c)(1),
(2), (4) Date: Aug. 27, 2004

(87) PCT Pub. No.: WO03/018806

PCT Pub. Date: Mar. 6, 2003

(65) Prior Publication Data

US 2005/0064413 A1    Mar. 24, 2005

(30) Foreign Application Priority Data

Aug. 24, 2001  (JP)  ............................. 2001-255198

(51) Int. Cl.
C07H 21/02 (2006.01)
(52) U.S. Cl. .................................................. 536/23.1
(58) Field of Classification Search .................... None
See application file for complete search history.

(56) References Cited

U.S. PATENT DOCUMENTS

| 5,424,186 A | 6/1995 | Fodor et al. | |
|---|---|---|---|
| 5,807,522 A | 9/1998 | Brown et al. | |
| 2004/0115625 A1* | 6/2004 | Ebner | 435/6 |

FOREIGN PATENT DOCUMENTS

| WO | WO00/23470 | * | 4/2000 |
|---|---|---|---|
| WO | WO/23470 A1 | | 4/2000 |

OTHER PUBLICATIONS

Miyajima et al., DNA Res, 4, 141-150, 1997.*
Shoni Naika, vol. 30, pp. 1483 (1988).
The New England Journal of Medicine, vol. 302 pp. 1524 (1980).
Medical Pediatric Oncology, vol. 31 pp. 113-115 (1998).
Shoni Geka (Pediatric Surgery), vol. 29, pp. 1425-1432 (1997).
Molecular Medicine, vol. 36, pp. 366 (1999).
Journal of Virology, 52:410-419 (1984).
Journal of Virology, 65:2968-2978 (1991).
Proc. Nat'l Acad. Sci. USA, 89:7742-7746 (1992).
Cell, 79:341-351 (1994).
The Journal of Biological Chemistry, vol. 275 (No. 48), pp. 37742-37751 (2000).
J. Biol. Chem., vol. 273 (No. 20), pp. 12415-12421 (1998).
Science, 272:263 (1996).
TIBS, 24(1):34-36 (1999).
Protein Engineering, 7:157-164 (1994).
Journal of Steriod Biochemistry & Molecular Biology, 74:319-324 (2000).
DATABASE EMBL 'Online! Jul. 12, 2002, "*Homo sapiens* mRNA; cDNA DKFZp762k117 (from clone DKFZp762K117)" XP002306406 retrieved from EBI accession No. EM_HUM:HSM805628, Database accession No. HSM805628.
DATABASE EMBL "Online! Mar. 17, 2000,"Human DNA sequence from clone RP11-146P9 XP002306407 retrieved EBI accession No. EM_HTG:AL161625; Database accession No. AL161625.
DATABASE EMBL Online! Jun. 14, 2000, "Human DNA sequence from clone RP11-108L4 on chromosome 9" XP002306408 retrieved from EBI accession No. EM_HUM:AL359314; Database accession No. AL359314.
Nase T et al: "Prediction of the Coding Sequences of Unidentified Human Genes VII. The Complete Sequences of 100 New CDNA Clones From Brain Which Can Code for Large Proteins In Vitro" DNA Research, Universal Academy Press, JP, vol. 4, No. 2, 1997, pp. 141-150, XP001052821; issn: 1340-2838.
-& DATABASE UniProt 'Online! Jan. 1, 1998, "KIAA0367 protein (Fragment)." XP002306409 retrieved from EBI accession No. UNIPROT:015073; Database accession No. 015073.
Ohira M: "Hunting the Subset-Specific Genes of Neuroblastoma: Expression Profiling and Differential Screening of the Full-Length-Enriched Oligo-Capping CDNA Libraries", Medical and Pediatric Oncology, Liss, New York, NY, US, vol. 35, No. 6, Dec. 2000, pp. 547-549, XP 002944158, ISSN: 0740-8226.
Choi D-K et al: "Fluorescent differential 1-9 display analysis of gene expression in apoptotic neuroblastoma cells" Gene, Elsevier Biomedical Press. Amsterdam, NL, vol. 223, No. 1-2, Nov. 26, 1998, pp. 21-31, CP004153574, ISSN: 0378-1119.

* cited by examiner

Primary Examiner—Shanon Foley
Assistant Examiner—Lei Yao
(74) Attorney, Agent, or Firm—Fitch, Even, Tabin & Flannery

(57) ABSTRACT

Human BMCC1 protein having an amino acid sequence set forth in SEQ ID NO:1 in the Sequence Listing and its variant protein, as well as human BMCC1 gene having a base sequence set forth in SEQ ID NO:2 in the Sequence Listing and its variant gene.

2 Claims, 7 Drawing Sheets

Fig.2

HUMAN BMCC1 GENE

CROSS-REFERENCED APPLICATIONS

This application is the National Stage of International Application PCT/P02/08520, filed Aug. 23, 2002, the complete disclosure of which is incorporated herein by reference, which designated the U.S. and that International Application was not published under PCT Article 21(2) in English.

TECHNICAL FIELD

This invention relates to a novel human BMCC1 protein with which part of BNIP2 has high homology as well as to a novel human BMCC1 gene.

BACKGROUND ART (Tumorgenesis and Genes)

Individual tumors exhibit distinct characteristic natures, and their biological properties are not necessarily identical even though the basic principle of oncogenesis is the same. Rapid advances in the understanding of cancer from a molecular biological and molecular genetic perspective in recent years have opened the way to an explanation of oncogenesis and tumor cell biology on the genetic level.

(Neuroblastomas)

Neuroblastoma is a pediatric cancer occurring in sympathetic gangliocytes and adrenal medullary cells which originate from cells of the peripheral sympathetic nervous system. Of these sympathetic nervous system cells, neural crest cells in the initial stage of development migrate to the abdomen, differentiating and maturing at sites where sympathetic ganglia are formed. Some of these cells migrate further to the adrenal bodies, penetrating through the adrenal cortex which is already in the process of formation, and reaching the medulla and forming medullary substance there. The neural crest cells also serve as a source of other peripheral nerve cells, differentiating into dorsal root ganglia (sensory nerves), skin pigment cells, thyroid C cells, some pulmonary cells, intestinal gangliocytes, and the like.

(Prognosis for Neuroblastoma)

Neuroblastoma is characterized by a varied clinical profile (Nakagawara, Shinkeigashu no Hassei to Sono Bunshi Kiko [Neuroblastoma Development and Molecular Mechanism], Shoni Naika 30, 143, 1998). For example, neuroblastoma occurring at less than one year of age has very favorable prognosis, with the majority undergoing differentiation and cell death, and spontaneous regression. Currently, most neuroblastomas discovered by a positive result in the commonly performed mass screening of 6-month-old infant urine are of the type which tend to undergo this spontaneous regression. On the other hand, neuroblastoma occurring at age 1 or higher is highly malignant and leads to death of the infant in the majority of cases. It is also hypothesized that a somatic mutation occurs in highly malignant neuroblastomas in infants older than one year of age, which are of monoclonal nature, whereas in naturally regressing neuroblastomas, the genetic mutation remains at only a germline mutation. See Knudson A G, et al.: Regression of neuroblastoma IV-S: A genetic hypothesis, N. Engl. J. Med. 302, 1254 (1980)).

(Tumor Markers which Allow the Diagnosis of Prognosis for Neuroblastoma)

With recent advances in molecular biology research, it has become clear that expression of the high affinity nerve growth factor (NGF) receptor TrkA is closely connected with control of differentiation and cell death. See Nakagawara A., The NGF story and neuroblastoma, Med. Pediatr. Oncol., 31, 113 (1998). Trk is a membrane-spanning receptor, existing as the three main-types, Trk-A, -B and -C.

These Trk family receptors play an important role in specific nerve cell differentiation and survival in the central nervous and peripheral nervous systems. See Nakagawara, et al., Shinkeigasaiboushu ni Okeru Neurotrophin Juyoutai no Hatsugen to Yogo [Expression of Neurotrophin Receptors and Prognosis in Neuroblastoma], Shoni Geka (Pediatric Surgery), 29: 425–432, 1997. The survival and differentiation of tumor cells is controlled by signals from Trk tyrosine kinase and Ret tyrosine kinase. In particular, the role of TrkA receptor is most significant, with TrkA expression being notably high in neuroblastomas with favorable prognosis, and its signals exerting a powerful control over survival and differentiation of tumor cells, and cell death (apoptosis). In neuroblastomas with unfavorable prognosis, on the other hand, TrkA expression is significantly suppressed, while tumor development is aided by a mechanism in which survival is promoted by signals from TrkB and Ret.

It has become clear that amplification of the neural oncogene N-myc has become clearly associated with the prognosis of neuroblastoma. See Nakagawara, Noushinkeishuyo no Tadankai Hatsugan [Multistage Oncogenesis of Cerebral and Neural Tumors], Molecular Medicine, 364, 366 (1999). This gene, first cloned in neuroblastoma, is ordinarily only present in a single copy per haploid set in normal cells and neuroblastomas with favorable prognosis, whereas it has been found to be amplified several dozen times in neuroblastomas with unfavorable prognosis.

Up till the present time, however, no oncogene other than N-myc is known to be expressed in neuroblastomas, and absolutely no genetic information other than that of N-myc has been known in relation to favorable or unfavorable prognosis.

DISCLOSURE OF THE INVENTION

This invention has been accomplished in light of the problems inherent in the prior art described above, and its object is to identify the base sequences of genes which are related to favorable or unfavorable prognosis of neuroblastoma, and to allow the provision of their genetic information as well as the functions of proteins which are the transcripts of the aforementioned genes.

As a result of conducting diligent research, the present inventors have examined the prognoses of neuroblastomas and have succeeded in constructing cDNA libraries from both clinical tissues with favorable prognosis and with unfavorable prognosis. Approximately 2400 clones were respectively obtained from these two types of cDNA libraries and were classified according to the prognosis of neuroblastoma (whether Favorable or Unfavorable).

Moreover, the present inventors found that the expression of a considerable number of the genes is enhanced only in clinical tissues of neuroblastoma with favorable prognosis among the classified genes and designated one of them as "BMCC1."

This invention provides a novel BMCC1 protein and the protein of the invention is one that is characterized by having an amino acid sequence set forth in SEQ ID NO:1 in the Sequence Listing or a salt thereof.

As used herein, the protein of this invention may have an amino acid sequence comprising a deletion, a substitution, an insertion or an addition of one or more amino acids in the amino acid sequence set forth in SEQ ID NO:1 in the Sequence Listing. It is also preferred that the protein or a salt thereof according to the invention have the aforementioned amino acid sequence and be provided with apoptosis-inducing activity.

The nucleic acid of this invention is one that is characterized by encoding the protein described above or a partial peptide.

Further, the nucleic acid of the invention is one that is characterized by having a base sequence set forth in SEQ ID NO:2 in the Sequence Listing.

As used herein, the nucleic acid of this invention may be an isolated nucleic acid characterized by hybridizing to the nucleic acid mentioned above or to its complementary nucleic acid under stringent conditions. In addition, it is preferred that the protein encoded by the nucleic acid be provided with apoptosis-inducing activity. The nucleic acid of the invention may also be one comprising a portion of a base sequence set forth in SEQ ID NO:2 in the Sequence Listing (which may be referred to as "nucleic acid fragment(s) of this invention).

Still further, the nucleic acid of this invention is preferably the one characterized in that its expression is enhanced in human neuroblastoma with favorable prognosis based on comparison between human neuroblastoma with favorable prognosis and human neuroblastoma with unfavorable prognosis.

BRIEF DESCRIPTION OF THE DRAWINGS

FIG. 2 is a figure corresponding to an electropherogram showing the results of determination of the expression levels of the BMCC1 gene in clinical samples of neuroblastomas with favorable prognosis and with unfavorable prognosis by semi-quantitative PCR.

BEST MODE FOR CARRYING OUT THE INVENTION

Figure 1:
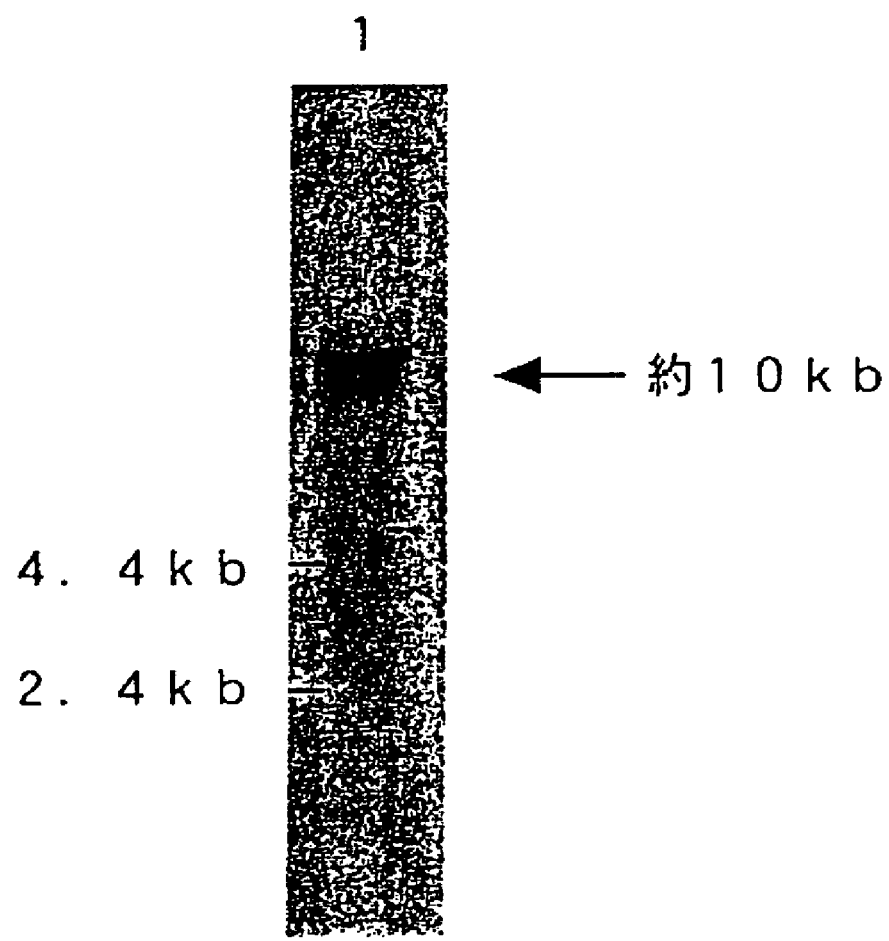
FIG. 1 is a figure corresponding to an electropherogram showing the results of the expression of the BMCC1 gene in a clinical sample of neuroblastoma with favorable prognosis as confirmed by Northern hybridization.

The term "nucleic acid(s)" as used in this specification refers to, for example, DNA or RNA, or polynucleotides derived therefrom which are active as DNA or RNA, and preferably refers to DNA and/or RNA.

The term "hybridize under stringent conditions" as used in this specification means that two nucleic acid fragments hybridize to each other under the hybridization conditions described by Sambrook, J. et al. in "Expression of cloned genes in E. coli", Molecular Cloning: A Laboratory Manual (1989), Cold Spring Harbor Laboratory Press, New York, USA, 9.47–9.62 and 11.45–11.61.

More specifically, the "stringent conditions" refers to hybridization at approximately 45° C., 6.0×SSC, followed by washing at 50° C., 2.0×SSC. The stringency may be selected by choosing a salt concentration in the washing step from approximately 2.0×SSC, 50° C. as low stringency to approximately 0.2×SSC, 50° C. as high stringency. Also, the temperature in the washing step may be increased from room temperature, or approximately 22° C. as low stringency conditions, to approximately 65° C. as high stringency conditions.

The term "isolated nucleic acid(s)" as used in this specification refers to a nucleic acid containing substantially no cellular substances or culture medium, if prepared by recombinant DNA techniques, or containing substantially no precursor chemical substances or other chemical substances, if prepared by chemical synthesis.

The term "favorable prognosis" as used in this specification refers to a condition of human neuroblastoma in which the tumor is localized or has become a regressing or benign sympathetic ganglion neoplasm, and is judged to have low malignancy based on N-myc or other tumor markers. According to a preferred embodiment of the invention, a favorable prognosis is a case of stage 1 or 2, with an onset age of less than one year and survival without recurrence for 5 or more years after surgery, and with no noted amplification of N-myc in the clinical tissue; however, there is no limitation to such specific cases. The term "unfavorable prognosis" as used in this specification refers to a condition of human neuroblastoma in which progression of the tumor has been observed, and it is judged to have high malignancy based on N-myc or other tumor markers. According to a preferred embodiment of the invention, an unfavorable prognosis is a case of stage 4, with an onset age of greater than one year, death within 3 years after surgery and noted amplification of N-myc in the clinical tissue; however, there is no limitation to such specific cases.

The novel human BMCC1 gene and protein of this invention have been found in the clinical tissues of human neuroblastomas with favorable prognosis and such gene and protein have the characteristics described below.

The human BMCC1 protein of this invention comprises an amino acid sequence set forth in SEQ ID NO:1 in the Sequence Listing. Further, the protein of this invention may be such that it has an amino acid sequence comprising a deletion, a substitution, an insertion or an addition of one or more amino acids in the amino acid sequence set forth in SEQ ID NO:1 in the Sequence Listing. In this case, it is preferred that the protein of the invention have the aforementioned amino acid sequence and be provided with apoptosis-inducing activity. The term "apoptosis-inducing activity" as used herein means the cell death which the cell itself actively induces under physiological conditions and the activity characteristically causes chromosome condensation of a nucleus, fragmentation of a nucleus, disappearance of microvilli from the cell surface or cytoplasm condensation.

This invention also encompasses salts of a protein of the invention. These salts are not particularly limited and, for example, preferred are a sodium salt, a potassium salt, a magnesium salt, a lithium salt and an ammonium salt.

Sugar chains are added to many proteins and the addition of a sugar chain may be adjusted by converting one or more amino acids. Therefore, the proteins of this invention include a protein the sugar chain addition of which has been adjusted in the amino acid sequence set forth in SEQ NO:1 in the Sequence Listing.

This invention also encompasses a nucleic acid having a base sequence encoding the human BMCC1 protein. The term "encoding a protein" as used herein means either of complementary double strands has a base sequence encoding the protein when DNA is double-stranded. The nucleic acids of this invention encompass a nucleic acid comprising a base sequence directly encoding the amino acid sequence set forth in SEQ ID NO:1 in the Sequence Listing and a nucleic acid comprising a base sequence complementary to said nucleic acid.

The human BMCC1 gene of this invention comprises a base sequence set forth in SEQ ID N:2 in the Sequence Listing.

Further, the nucleic acid of the invention may be a nucleic acid hybridizing to the nucleic acid comprising a base sequence set forth in SEQ ID NO:2 under stringent conditions. The base sequence is not particularly limited insofar as it satisfies this condition. Still further, the nucleic acids of the invention encompass a nucleic acid comprising a base sequence complementary to the nucleic acid hybridizable under the stringent conditions mentioned above. Specifically there is mentioned a nucleic acid comprising deletions, substitutions, insertions or additions in some bases of the nucleic acid comprising a base sequence set forth in SEQ ID NO:2 or a nucleic acid complementary to said nucleic acid. As used herein, the deletion, the substitution, the insertion and the addition include not only a short deletion, substitution, insertion and addition with 1 to 10 bases, but also a long deletion, substitution, insertion and addition with 10 to 100 bases.

Moreover, it is preferred that the nucleic acid of this invention be a nucleic acid comprising deletions, substitutions, insertions or additions in some of the bases mentioned above and it be provided with apoptosis-inducing activity. The term "apoptosis-inducing activity" as used herein means the cell death which the cell itself actively induces under physiological conditions and the activity characteristically causes chromosome condensation of a nucleus, fragmentation of a nucleus, disappearance of microvilli from the cell surface or cytoplasm condensation.

The present inventors have found that the amino acid sequence of BMCC1 comprises 2724 amino acids and a partial amino acid sequence thereof has about 57% homology to 314 amino acids which are part of Bcl-2/Adenovirus E1B 19 kDa interacting protein 2 (BNIP2) Moreover, the present inventors have found that BMCC1 has a coiled-coil domain, a transmembrane domain, and a nucleus translocation signal domain.

(E1B 19 kDa Protein)

E1B 19 kDa protein is a protein encoded by the E1B gene of adenovirus. It is known that the adenovirus which has a mutation in this gene causes strong cell damage to the host and induces decomposition of DNA. (White E. et al.: Mutation in the gene encoding the adenovirus early region 1B 19,000-molecular-weight tumor antigen causes the degradation of chromosomal DNA. J. Virol. 52 (2), 410–419 (1984)). It has been reported that this cell damage is apoptosis induced by E1A protein that is first expressed in adenovirus-infected cells and the E1B 19 kDa protein suppresses the apoptosis. (White E. et al.: Adenovirus E1 19-kilodalton protein overcomes the cytotoxicity of E1A proteins. J. Virol. 65(6), 2968–2978 (1991)). In subsequent studies it has been reported that the E1B 19 kDa protein is functionally homologous to Bcl-2. (Rao L. et al.: The adenovirus E1A proteins induce apoptosis, which is inhibited by the E1B 19-kDa and Bcl-2 proteins. Proc. Natl. Acad. Sci. USA 89 (16), 7742–7746 (1992)).

(Structure and Function of BNIP)

Bcl-2/Adenovirus E1B 19 kDa interacting protein (BNIP) has been identified as a protein binding to the E1B 19 kDa protein. (Boyd J M et al: Adenovirus E1B 19 kDa and Bcl-2proteins interact with a common set of cellular proteins. Cell 79 (2), 341–351 (1994)). It has been suggested that BIP suppresses apoptosis by interacting with the E1B 19 kDa protein or Bcl-2. Three types of BNIPs have been identified thus far. One of them, BNIP1, has a transmembrane region at its C-terminus and is localized in mitochondria, nuclear membrane and endoplasmic reticulum. It has also been reported that BNIP1 has a BH3 region, induces apoptosis and forms a heterodimer with Bcl-XL.

There has been a report on BNIP2 that it is localized in nuclear membrane and endoplasmic reticulum and it shows the phenomena of suppressed expression by estrogen in SK-ER3, a neuroblastoma cell line, and transient enhanced expression in the maturation process of a rat fetus brain. Recently, it has been suggested that BNIP2 is involved in the signal transudation by binding to Cdc42 which is a GTP-binding molecule and to GTPase-activating protein for Cdc42 (Cdc42GAP). Moreover, it has been reported that BNIP2 is phosphorylated by fibroblast growth factor (FGF)-receptor tyrosinekinase and its binding to Cdc42 or Cd42GAP is inhibited. (Low BC et al.: The BNIP-2 and Cdc42GAP homologydomain of BNIP-2 mediates its homophilic association and heterophilic interaction with Cdc42GAP. J. Biol. Chem. 275(48), 37742–37751 (2000).)

It has also been known that BNIP3 is a protein of the apoptosis-inducing type with a BH3 region and has a transmembrane region at its C-terminus and that it is localized in mitochondria. (Yasuda M et al.: Adenovirus E1B-19 K/Bcl-2 interacting protein BNIP3 contains BH3 domain and mitchondrial targeting sequence. J. Biol. Chem. 273 (20), 12415–12421 (1998).) In addition, BNIP3 has been reported to be induced strongly upon exposure under hypoxia conditions for a prolonged period of time.

Apoptosis is frequently observed in neuroblastomas with favorable prognosis. Thus, when homology in the overlapping part between BMCC1 and BNIP2 is considered, BMCC1 is presumed to have the function of being able to participate in the apoptosis induction.

Further, the BMCC1 gene is specifically expressed in the genes with favorable prognosis and is specifically expressed in the differentiated cells. In highly likelihood the gene has the function of directing the neuroblastoma to favorable prognosis.

In summary, the human BMCC1 gene and protein according to this invention have been described. The embodiments that will enable the provision of various kinds of information relating to the gene and the protein will be explained below.

(1) Probes for Use in Hybridization

In the utilization of the nucleic acid or its fragment according to this invention can be used as a probe for hybridization to detect the BMCC1 gene expressed in any tissues and cells. The nucleic acid or its fragment according to this invention can also be used as probes for hybridization in order to determine gene expression in several of tumors and normal tissues, to identify the distribution of the gene expression.

When the nucleic acid or its fragment according to this invention is used as a probe for hybridization, there are no particular limitations on the actual method of hybridization. As preferred methods there may be mentioned, for example, Northern hybridization, Southern hybridization, colony hybridization, dot hybridization, fluorescence in situ hybridization (FISH), in situ hybridization (ISH), DNA chip methods, and microarray methods.

As one application example of the hybridization, the nucleic acid or its fragment according to this invention can be used as a probe for Northern hybridization to measure the length of mRNA or to quantitatively detect gene expression in an assayed sample.

When the nucleic acid or its fragment according to this invention is used as a probe for Southern hybridization, it enables the detection of the presence or absence of the base sequence in the genomic DNA of an assayed sample.

The nucleic acid or its fragment according to this invention can also be used as a probe for fluorescence in situ hybridization (FISH) to identify the location of the gene on a chromosome.

The nucleic acid or its fragment according to this invention can also be used as a probe for in situ hybridization (ISH) to identify the tissue distribution of gene expression.

When the nucleic acid or its fragment according to this invention is used as a probe for hybridization, a base length of at least 20 is necessary; and among portions of the base sequences disclosed in this specification, a nucleic acid having 20 or more contiguous bases is preferably used. More preferably, one having 40 or more bases is used and most preferably one having 60 or more bases is used.

Nucleic acid probe techniques are well known to one skilled in the art, and for example, conditions suitable for hybridization between a probe of specific length according to the invention and the target polynucleotide may be readily determined. In order to obtain hybridization conditions optimal to probes of varying lengths, Sambrook et al. "Molecular Cloning: A Laboratory Manual, 2nd Edition, Cold Spring Harbor (1989) may be followed for such manipulations which are well known to one skilled in the art.

The probe according to this invention may preferably be labeled for use in an easily detectable fashion. The detectable label may be any type or portion which can be detected either visually or using devices. As commonly used detectable labels, there may be mentioned radioactive isotopes such as $^{32}P$, $^{14}C$, $^{125}I$, $^{3}H$ and $^{35}S$. Biotin-labeled nucleotides may be incorporated into DNA or RNA by nick translation, or chemical or enzymatic means. The biotin-labeled probes are detected after hybridization using labeling means such as avidin/streptavidin, fluorescent labels, enzymes, gold colloidal complexes or the like. The nucleic acid may also be labeled by binding with a protein. Nucleic acid cross-linked to a radioactive or fluorescent histone single-stranded DNA binding protein may also be used.

(2) Primers for Use in PCR

For other possible methods of detecting genes, any nucleic acid (DNA) sequence contained in the nucleic acid of this invention can be used as a primer in a polymerase chain reaction (PCR). For example, RNA may be extracted from a sample to be assayed, and the gene expression can be semi-quantitatively measured by RT-PCR. This may be carried out by a method well known to one skilled in the art. For example, "Molecular Cloning: A Laboratory Manual," (T. Maniatis, Cold Spring Harbor Laboratory Press) or Idenshibyo Nyumon [Introduction to Genetic Diseases] (Takahisa, S.: Nankodo Publishing) may be Followed.

When the nucleic acid or its fragment according to this invention is used as a PCR primer, a base length of 10 to 60 is necessary; and among portions of the base sequences disclosed in this specification, the nucleic acid having 10 to 60 contiguous bases is preferably used. More preferably, one having 15 to 30 bases is used. Generally, a primer sequence with a GC content of 40–60% is preferred. Also, there is preferably no difference in the Tm values of the two primers used for amplification. The primer has such base sequence that there is no annealing at the 3' ends of the primers and no secondary structure is formed in the primers.

(3) Nucleic Acid Screening

The nucleic acid or its fragment according to this invention can also be used to detect the expression distribution of the gene which is expressed in various tissues or cells. The detection of expression distribution of the target gene can be accomplished, for example, by using the nucleic acid or its fragment according to this invention as a probe for hybridization or as a primer for PCR.

The expression distribution of the gene can also be detected using a DNA chip, microarray or the like. That is, the nucleic acid or its fragment according to the invention may be directly attached to the chip or array. RNA extracted from a cell may be labeled with a fluorescent substance or the like, hybridized thereto, and an analysis can be made of the type of cells with high expression of the gene. There is known a method by which nucleic acids or others (DNA) are spotted to a substrate for the purpose of attaching them to a chip or array by using a high precision dispenser (for example, see U.S. Pat. No. 5,807,522). RNA extracted from a subject specimen may be labeled with a fluorescent substance or the like, hybridized thereto, and an analysis can be made of the type of tissue cells with high expression of the gene. The DNA attached to the chip or the array may be the reaction product of PCR using the nucleic acid or its fragment according to the invention. As an alternative method, the nucleic acid fragment of the invention (DNA fragment) may be directly synthesized on a substrate to form a DNA chip or a DNA array (See, for example, U.S. Pat. No. 5,424,186).

(5) Methods of Diagnosing Tumor Prognosis and Tumor Markers to be Used Therefor

The nucleic acid or its fragment according to this invention can be used as a probe for hybridization, or as a primer for PCR to determine the presence or absence of enhancement in the gene expression in sample cells, which enables the identification of prognosis. To determine the presence or absence of enhancement in the gene expression, any method that utilizes probes capable of hybridizing to the nucleic acid or its fragment according to the invention is provided for use. Specifically, prognosis can be diagnosed as favorable if the amount of nucleic acid hybridizing to the probe is increased in the sample cell. When the nucleic acid is used as a primer for PCR, RNA is extracted from the sample to be assayed and the gene expression can be semi-quantitatively measured by the RT-PCR method.

(6) Antisense Oligonucleotides

According to another embodiment of this invention there are provided antisense oligonucleotides and nucleic acids encoding the antisense oligonucleotides. As will be considered in practicing this invention, the antisense oligonucleotides and the nucleic acids encoding the antisense oligonucleotides may readily be prepared such that they can bind to RNA corresponding to the gene of this invention and can thereby inhibit the synthesis of RNA.

(7) Gene Therapy

According to a further embodiment of this invention, there are provided nucleic acids constituting therapeutic genes to be used in gene therapy. As will be considered in practicing this invention, the nucleic acid constituting the gene of the invention may be transferred into a vector for use in gene transportation, whereby the transgene can be expressed by an arbitrary expression promoter and can be used for the gene therapy of cancers, for example. The vectors and the expression promoters will be described below.

1. Vectors

The transferable viral vectors may be prepared from DNA viruses or RNA viruses. They may be any viral vector of an MOMLV vector, a herpes virus vector, an Adenovirus vector, an AAV vector, a HIV vector, a SIV vector, a Seidai virus vector and the like. One or more proteins among the constituent protein group of a viral vector are substituted by the constituent proteins of a different species of virus, or alternatively a part of the nucleic acid sequence constituting genetic information is substituted by the nucleic acid sequence of a different species of virus to form a viral vector of the pseudo-type which can also be used in this invention. For example, there is mentioned a pseudo-type viral vector wherein the Env protein (an envelop protein of HIV) is substituted by the VSV-G protein (an envelop protein of vesicular stomatitis virus or VSV) (Naldini L., et al., Science 272, 263–1996). Further, viruses having a host spectrum other than human are usable as the viral vector insofar as they are efficacious. As for the vectors other than those of viral origin, there may be used complexes of calcium phosphate and nucleic acid, ribosomes, cation-lipid complexes, Seidai virus liposomes, polymer carriers having polycation as the backbone main chain and others. In addition, methods such as electroporation and gene guns may be used as a gene transfer system.

2. Expression Promoters

As for the expression cassettes to be used for the therapeutic gene, any cassettes without any particular limitations may be used insofar as they can cause genes to express in the target cells. One skilled in the art can readily select such expression cassettes. Preferably, they are expression cassettes capable of gene expression in the cells derived from an animal, more preferably, expression cassettes capable of gene expression in the cells derived from a mammal, and most preferably expression cassettes capable of gene expression in the cells derived from a human. The gene promoters that can be used as expression cassettes include: for example, virus-derived promoters from an Adenovirus, a cytomegalovirus, a human immunodeficiency virus, a simian virus 40, a Rous sarcoma virus, a herpes simplex virus, a murine leukemia virus, a sinbis virus, a hepatitis type A virus, a hepatitis type B virus, a hepatitis type C virus, a papilloma virus, a human T cell leukemia virus, an influenza virus, a Japanese encephalitis virus, a JC virus, parbovirus B19, a poliovirus, and the like; mammal-derived promoters such as albumin, SRα, a heat shock protein, and an elongation factor; chimera type promoters such as a CAG promoter; and the promoters whose expression can be induced by tetracyclines, steroids and the like.

(8) Drugs

According to a still further embodiment of this invention, there are provided therapeutic proteins and peptides. As will be considered in practicing this invention, the protein of the invention and the peptide of the invention may be prepared according to the formulation method of choice and may be used through any desired route of administration and at any desired dosage age as an antitumor agent or an antimetastatic agent, for example.

1. Preparation Method

The drug according to this invention may be prepared as a recombinant viral vector containing a therapeutic gene that is designed for therapeutic purposes. More specifically, a recombinant virus vector comprising the BMCC1 gene may be prepared by dissolving it in an appropriate solvent such as water, physiological saline or an isotonized buffer solution. Alternatively, the BMCC1 protein produced by any desired method may be dissolved in an appropriate solvent such as water, physiological saline or an isotonized buffer solution to prepare the vector similarly. Here, polyethylene glycol, glucose, various amino acids, collagen, albumin or the like may be then added as protective materials for the preparation.

2. Administration Method and Dosage

There are no particular limitations on the method of administrating the drug according to this invention. For example, parental administration, including injection is preferably carried out. The use level of the drug according to the invention varies depending on the method of use, the purpose of use, etc; and one skilled in the art can easily select as appropriate and optimize it. In the case of injection, for example, the daily dosage is preferably administered at about 0.1 μg/kg to 1000 mg/kg per day, and more preferably at about 1 μg/kg to 100 mg/kg per day.

(9) Antibodies, Antisense, Ribozymes and TFO

In accordance with a still another embodiment of this invention, an antibody to suppress the activity of the protein of the invention and base sequences including antisense to suppress the expression of the gene of the invention, ribozyme and TFO are provided. As will be considered in practicing this invention, nucleic acids encoding antisenses, ribozymes and TFOs according to the invention can be transferred into a vector used as a gene carrier; the transgene can be expressed by any suitable expression promoter and can be used, for example, to establish a primary culture cell line or to construct a cancer model animal.

(10) Genetically Modified Animals

In accordance with a yet another embodiment of this invention, a nucleic acid to knock out the expression of the gene of the invention and a knockout animal (e.g., knockout mouse) are provided. There are provided a transgenic animal (e.g., transgenic mouse) where the gene has been forcedly expressed and a genetically modified animal into having an introduced mutant gene obtained by introducing an arbitrary mutation (such as a point mutation or deletion) into the gene. This genetically modified animal can be used to construct a cancer model animal, foe example.

As described above, by utilizing the BMCC1 gene or the BMCC1 protein according to this invention or the information obtainable therefrom, it will be possible to detect the BCC1 gene in a clinical tissue, which then will allow the diagnosis of favorable or unfavorable prognosis. Further, by utilizing the BMCC1 gene or the BMCC1 protein or the information obtainable therefrom, it will be possible to design tumor markers that can be used in the diagnosis for prognosis and the aforementioned method.

EXAMPLES

This invention will now be explained in greater detail by way of the examples; however, the invention will not be restricted to those examples.

Preparation Example 1) Clinical Tissues of Neuroblastomas

The clinical tissue specimens of neuroblastoma were frozen immediately after surgical extraction and then preserved at −80° C. Prognosis of the samples was carried out based on the following criteria.
Favorable Prognosis:
Stage 1 or 2
Age of onset less than one year
Survival for longer than 5 years after surgery without recurrence
No amplification of MYCN
Unfavorable Prognosis:
Stage 4
Age of onset older than 1 year
Death within 3 years after surgery
Amplification of MYCN
The amplification of MYCN was confirmed in the following manner. The clinical tissue obtained was thinly sliced with a scalpel and then thoroughly homogenized after addition of 5 ml of TEN buffer (50 mM Tris-HCl (pH=8.0)/1 mM EDTA/100 mM NaCl). Upon adding 750 μl of SDS (10%) and 125 μl of proteinase K (20 mg/ml) to the mixture, it was gently stirred and allowed to stand at 50° C. for 8 hours. This was followed by phenol/chloroform treatment and finally ethanol precipitation to obtain purified genomic DNA. A 5 μg portion of the obtained genomic DNA was completely digested with the restriction endonuclease EcoRI (NEB Inc.), and an MYCN probe was used to determine amplification of MYCN by Southern hybridization (Sambrook J et al.: Molecular Cloning).

Preparation Example 2) Human-Derived Cancer Cell Lines

The following cell lines were used as human-derived cancer cell lines.
Cell Lines Derived from Neuroblastoma (MYCN Amplification)
SY5Y, NB69, SK-N-AS, OAN, and SK-N-SH
Cell Lines Derived from Neuroblastoma (No MYCN Amplification)
RISA, GOTO, P3, SK-N-BE, CHP901, NGP, RTBM1, IMR32, NMB, LAN5, TGW, CHP134, and KCN
Cancer Cell Lines Derived from Other Tissues
OST (osteosarcoma), SAOS-2 (osteosarcoma), NOS-1 (osteosarcoma), RMS-Mk (rhabdomyosarcoma), ASPS-KY (focal soft part sarcoma), COLO320 (colon adenocarcinoma), SW480 (colon adenocarcinoma), LOVO (colon adenocarcinoma), HepG2 (hepatic carcinoma), MB453 (breast cancer), MB231 (breast cancer), G361 (malignant melanoma), G32TG (malignant melanoma), A875 (malignant melanoma), TTC2 (thyroid cancer), KATO3 (gastric cancer), ECF10 (esophageal cancer), ASPC-1 (metastatic pancreas adenocarcinoma), A549 (lung cancer), NT2 (teratoma), and HeLa (cervical carcinoma)
All the cancer cell lines except for HeLa were cultured in a RPMI-1640 medium containing 10% FBS, 50 units/ml penicillin, and 50 μg/ml streptomycin. HeLa cells were cultured in a DMEM medium containing 10% FBS, 50 units/ml penicillin, and 50 μg/ml streptomycin. All the cancer cell lines, including HeLa, were cultured by incubation under conditions at 37° C. and 5% $CO_2$ concentration.

Example 1) Extraction of Total RNA from Clinical Neuroblastoma Tissues

The extraction of total RNA from a human clinical neuroblastoma tissue was conducted using a Total RNA Extraction Kit (Qiagen, Inc.). The extracted total RNA was purified with phenol/chloroform, after which its concentration was determined.

Example 2) Extraction of Total RNA from Cancer Cell Lines

The extraction of total RNA from cancer cell lines was conducted following conventional guanidine treatment (Sambrook et al: Molecular Cloning). The extracted total RNA was purified with phenol/chloroform, after which its concentration was determined.

Example 3) Construction of cDNA LIBRARY

The cDNA library was constructed from the total RNA, which was prepared from the clinical tissue of neuroblastoma in Example 1, according to the oligo-capping method (Sugano S et al: Gene 138 (1–2): 171–174 (1994)). The obtained cDNA library was used for transformation into *E. coli* (TOP-10, Invitrogen Corporation).

Example 4) Analysis of Both End Sequences of cDNA

Plasmid DNA was extracted from the *E. coli* cell prepared in Example 3 and both end sequences of the cDNA were determined using a DNA Sequencing Kit (ABI). There were combined 600 ng of plasmid DNA, 8 μl of premix (kit accessory) and 3.2 pmol of primers, and sterile distilled water was added to a total of 20 μl. After denaturing the mixture at 96° C. for 2 minutes, a cycle of 96° C. for 10 seconds, 50° C. for 5 seconds and 60° C. for 4 minutes was repeated 25 times for reaction. Purification was then carried out through ethanol precipitation. Electrophoresis was conducted on polyacrylamide gel under denaturing conditions to perform sequencing. ABI377 (ABI) was used for sequencing.

Example 5) Homology Search Using Database

An Internet-mediated DNA sequence homology search was conducted for the cDNA sample of which the both end-sequences were analyzed in Example 4. The homology search was conducted using the BLAST of the NCBI (National Center of Biotechnology Information, USA). As a result of the homology search, nbla219 (one of the cDNA samples) showed high homology to the genomic sequence on human chromosome No. 9 (GeneBank Accession No. AL161625).

Example 6) Cloning of the Full-Length nbla219

For the genomic sequence obtained in Example 5, its gene transcription sequence was deduced using GENESCAN (Burge C et al.: 1997, 1998) and FGENESH (Salamov A A et al.: 1999). Based on the putative sequence the cloning of the full-length of nbla219 was conducted according to the method described below.

Specifically, 15 μg of total RNA extracted from a clinical tissue of neuroblastoma with favorable prognosis was reverse transcribed to cDNA using superscript II reverse transcriptase (GIBCO). The reverse-transcribed cDNA (2 μl), 5 μl of sterile distilled water, 1 μl of 10×rTaq buffer (Takara Shuzo Co., Ltd.), 1 μl of 2 mM dNTPs, 0.5 μl each of the synthesized primer set and 0.5 μl of rTaq (Takara Shuzo Co., Ltd.) were combined. After denaturing the mixture at 95° C. for 2 minutes, a cycle of 95° C. for 15 seconds, 58° C. for 15 seconds and 72° C. for 20 seconds was repeated 35 times, and then the mixture was allowed to stand at 72° C. for 20 minutes for PCR reaction. The bands amplified by PCR were subcloned into a pGEM-T easy vector (Promega Corporation) and the base sequences were determined according to a standard method (Sanger F. et al.: Proc. Natl. Acad. Sci. USA 74: 5463–5467 (1977)). AB1377 (ABI) was used for analysis and both strands of all the base sequence were analyzed.

Oligonucleotides having the base sequences described below were used as the primers.

```
FW1:    5'ACAGCAATATTACCAGTGAC3'     (SEQ ID NO: 3)
FW2:    5'AGTTTGGTTTTGATGTCCTC3'     (SEQ ID NO: 4)
FW3:    5'AGAACCCTTGCCTAGAACTG3'     (SEQ ID NO: 5)
FW4:    5'GACTGTGGCTGTGATGAGAT3'     (SEQ ID NO: 6)
FW5:    5'AAGGAAGTCATCAACAGGAG3'     (SEQ ID NO: 7)
FW6:    5'CAATAGCCGGACATCCTCAA3'     (SEQ ID NO: 8)
FW7:    5'ATGATTTGGACTGGGATGAC3'     (SEQ ID NO: 9)
FW8:    5'GCTCTCTTGCTGTCACTTTC3'     (SEQ ID NO: 10)
FW9:    5'TAAGGGGTCTGAAAATAGCC3'     (SEQ ID NO: 11)
FW10:   5'GATCGCAAAACTCCTACATT3'     (SEQ ID NO: 12)
FW11:   5'CAGAGCTTGGGATTCATTGA3'     (SEQ ID NO: 13)
FW12:   5'TAAGTTCTTGGTCACAGCTG3'     (SEQ ID NO: 14)
FW13:   5'GCCAGCAGAGAATGAGAATA3'     (SEQ ID NO: 15)
FW14:   5'TTTTAAAGCAGCCCTGATCC3'     (SEQ ID NO: 16)
FW15:   5'CCAGCTTGTAAAATTAGACC3'     (SEQ ID NO: 17)
FW16:   5'CAGATTACAGCAGTGGAGAA3'     (SEQ ID NO: 18)
FW17:   5'CACGCAGAGGAAAATAGTTG3'     (SEQ ID NO: 19)
FW18:   5'ACCAGTTGACAGAAGAATCC3'     (SEQ ID NO: 20)
FW19:   5'ATCCACATTTATCCACAGAG3'     (SEQ ID NO: 21)
FW20:   5'CTTTGGAGGAAGATTCTCTG3'     (SEQ ID NO: 22)
FW21:   5'AGAGCCTGAGCAGATAAAAT3'     (SEQ ID NO: 23)
FW22:   5'TGTTCTTGGGCCATAGTGAG3'     (SEQ ID NO: 24)
FW23:   5'GATATCAAGACCAAATGGAC3'     (SEQ ID NO: 25)
FW24;   5'AATATACGGCCGAAGAGGAA3'     (SEQ ID NO: 26)
FW25:   5'CAGATGATTGACAGACGGTT3'     (SEQ ID NO: 27)
RV1:    5'TTCTCCAGACCATGCATGTT3'     (SEQ ID NO: 28)
RV2:    5'GAGCCTGGTAACATGAATGA3'     (SEQ ID NO: 29)
RV3:    5'TCAATTAGTCTCCCTTCCTG3'     (SEQ ID NO: 30)
```

-continued

```
RV4:    5'CTCACCATCTGCTTTCAAAC3'     (SEQ ID NO: 31)
RV5:    5'ATATCTTGCTTCCCTAGGTC3'     (SEQ ID NO: 32)
RV6:    5'GTCACCACCATACAGGAAGT3'     (SEQ ID NO: 33)
RV7:    5'CTCCTACCGGCAAATAAACG3'     (SEQ ID NO: 34)
RV8:    5'CTCACTATGGCCCAAGAACA3'     (SEQ ID NO: 35)
RV9:    5'GTCCATTTGGTCTTGATATC3'     (SEQ ID NO: 36)
RV10:   5'TTCCTCTTCGGCCGTATATT3'     (SEQ ID NO: 37)
RV11:   5'AACCGTCTGTCAATCATCTG3'     (SEQ ID NO: 38)
RV12:   5'AAAGGTCGTGTCACAGCAAG3'     (SEQ ID NO: 39)
RV13:   5'ATAAAAGGTCGTGTCACAGC3'     (SEQ ID NO: 40)
RV14:   5'ATGCTCTCTGGAATGTGGAT3'     (SEQ ID NO: 41)
RV15:   5'ATGATGCTCTCTGGAATGTG3'     (SEQ ID NO: 42)
RV16:   5'GGCAAAATAGGAAAGTAC3'       (SEQ ID NO: 43)
RV17:   5'TAAACACCAGTCTAAGGG3'       (SEQ ID NO: 44)
```

Example 7) Registration of the BMCC1 Full-Length Sequence

The gene sequence of BMCC1 obtained in Example 6 was registered with DDBJ, GeneBank, EMBL. The accession number was AB050197.

Example 8) Northern Hybridization

The total RNA (25 μg) was electrophoresed using 1% agarose gel under denaturing conditions. The total RNA electrophoresed was transferred to a nylon membrane from the agarose gel according to the capillary method. An about 1.5 kb-probe was designed after the base sequence of human BMCC1 and Northern hybridization was carried out. The final washing was conducted with 0.1×SCC, 0.1% N-lauroyl sarcosine at 65° C. for 30 minutes. The base sequence of the probe used (SEQ NO:45) is shown below. The results obtained are also shown in FIG. 1.

```
GTCGACATCTTTGCACAGGTGATTGAGTTTCTCTGA
CCTCATTGCTTCACCTCTGTCTCCTCCCGTCCTTCC
GCACGTGCCCACACACACGCAGTTCAGCCCTCTTTC
CTCCATAAGCCTCCATCGTTTTCTCTTTTCTCCTCT
TGATCCTTTCAAGCGAGTATCTTGTTGAATTGTATG
TTCTGTTGGATCTCCTCCTTCATAACATCTGGCTTG
TTGGACAGAAAAACCCTACAGCCCACCCCCTCCCAC
AGCCCACCTCCACTTTTGAAAGCCCAAATTACACCT
CTCCCAGAACACAGTGTTGACGTAAATACAGTTACC
CAATATTCCTGTTTGTTCACCTATTTGCTACTTTCA
CTCAGTAGCATCCCATTTTGTAAAATGAATTCCATG
GTCACCCTGTCACAGGAAGTAATGAAAAATCCAGTG
```

-continued

```
TTCAGTGTAGTGGTGCAAACCTGAGGGCATAGAGCT
GTTCATAGAGGGCTCTTGTTATAGCCAAACAGACAC
AGCAACAATCTCACCATTTATATATATATTTTTAAC
TTGTCCAGCTCATCTATGGAAAACTACTCAGGTGGT
ATGCTGTTTGAAGCCTCATCTTCCTACATGAAAATT
ATGGGCATTTGTCCCAATGATTTTGTTTCAGCTGTT
CTGTAGGCTGCATAACCACTCTGATATTTAGGTATC
TGCTATTTTATTATCTTAAAAGACAAATTAATTTAA
TTGCATGTGCTAGGGAAAAGCTACCATGTACATTCA
CCCCAAGTAAATAGAATCCTAGATGAATCCTAGAAA
AATAATCCCTAAGCAGATAGGTAGACAGAGGTAAAC
ATTCACATGATTTAGCTCTCTAGCTCTTGCACTCTG
AACATTCTTGCTTTGGTTCTGACTTCTGGGAACTGC
TTTGCATTTCTCCTATAGATCTGTAGTTAAGGGAAC
CAAGGGGTCATTGGGGCAAAAGCATTGTTTCTCAAA
GCTCCTTGATTAAGAGAAAGAACAGAATTTGCACAG
AAGATAGTGTCAAGGAGTGAGAAAGTTTGTTTGAGG
GCAGTAGCTCAGTGTGGAAGAAAATCCTGAAGTTTC
TGTTGAAGCCATACAATGTTCTATGGGGTTACTCTC
TAAGACATTCTCTGAGGTGTGTGAGGAAGTCACTAC
TCCTAGCCTTTGTTAAGATGTAATTTTAAATATTCA
GTTATGGTACTATGTTTGCAACTCTCGTCTTATCAC
AATGCCTCAGTAGTTTGTTCCCTTAGAAACATTTAG
ATGTGCACAAATTAATCTTTTATATATCTAAAGGTT
TTTCTATCATGCATTGGATTGCTCAGAATAAAGTGT
CTGTTAGACTTCGTTTTGGTAAATAAATTCTCCATA
ATGTAGATTAATAATATAAAAGTCTTTAATGACACA
ATATATCTATATAGCCTCACTGTATAATTCAGAAAT
AAAAATTGATTCTGC
```

Example 9) Semi-Quantitative RT-PCR

All semi-quantitative RT-PCR reactions were performed in the manner described below.

(Reverse Transcription (RT))

The extracted total RNA (5 μg) was reverse-transcribed into cDNA using a Superscript II reverse transcriptase (GIBCO).

(PCR)

PCR was performed with rTaq (Takara Shuzo Co., Ltd.). The reverse-transcribed cDNA (2 μl), 5 μl of sterile distilled water, 1 μl of 10×rTaq buffer, 1 μl of 2 mM dNTPs, 0.5 μl each of the synthesized primer set and 0.5 μl of rTaq were combined. After denaturing the mixture at 95° C. for 2 minutes, a cycle of 95° C. for 15 seconds, 58° C. for 15 seconds and 72° C. for 20 seconds was repeated 35 times, and then the mixture was allowed to stand at 72° C. for 20 minutes for PCR reaction. For the primers of BMCC1, the oligonucleotides having the base sequences described below were used.

```
FW:  5'CAATAGCCGGACATCCTCAA3'     (SEQ ID NO: 46)
RV:  5'TTCTCCAGACCATGCATGTT3'     (SEQ ID NO: 47)
```

GAPDH was used as the positive control. Primers are shown below.

```
FW:  5'CTGCACCAACAATATCCC3'       (SEQ ID NO: 48)
RV:  5'GTAGAGACAGGGTTTCAC3'       (SEQ ID NO: 49)
```

Figure 2:
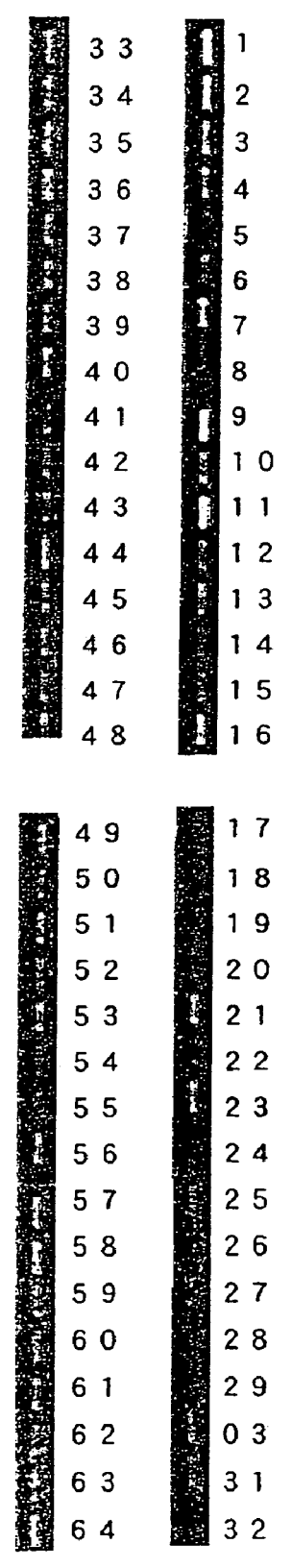
Figure 3:
FIG. 3 is a figure corresponding to an electropherogram showing the results of determination of the expression levels of the BMCC1 gene in normal human tissues by semi-quantitative PCR.

Example 10) Determination of Gene Expression Levels that are Dependent on Neuroblastoma Clinical Tissues with Favorable Prognosis by Semi-Quantitative PCR RT-PCR was performed on the total RNAs of neuroblastomas with favorable prognosis and with unfavorable prognosis obtained in Example 1 under the conditions described in Example 9. These reaction solutions were electrophoresed on 2.5% agarose gel. The results confirmed that the expression of the BMCC1 gene was specific for the neuroblastoma clinical tissues with favorable prognosis. Results are shown in FIG. 2. Here, in FIG. 2 the samples in each lane are as follows:

Lanes 1–16: the expression of human BMCC1 in neuroblastoma clinical samples with favorable prognosis Lanes 17–32: the expression of human BMCC1 in neuroblastoma clinical samples with unfavorable prognosis Lanes 33–48: the expression of GAPDH in neuroblastoma clinical samples with favorable prognosis Lanes 49–64: the expression of GAPDH in neuroblastoma clinical samples with favorable prognosis Example 11) Determination of Tissue-Dependent Gene Expression Levels by Semi-Quantitative PCR mRNAs of normal human tissues (Clontech) were used to perform RT-PCR under the conditions described in example 9. These reaction solutions were electrophoresed on 2.5% agarose gel. The results confirmed that the expression of the BMCC1 gene expression was tissue-specific among the normal human tissues. Results are shown in FIG. 3.

Figure 4:
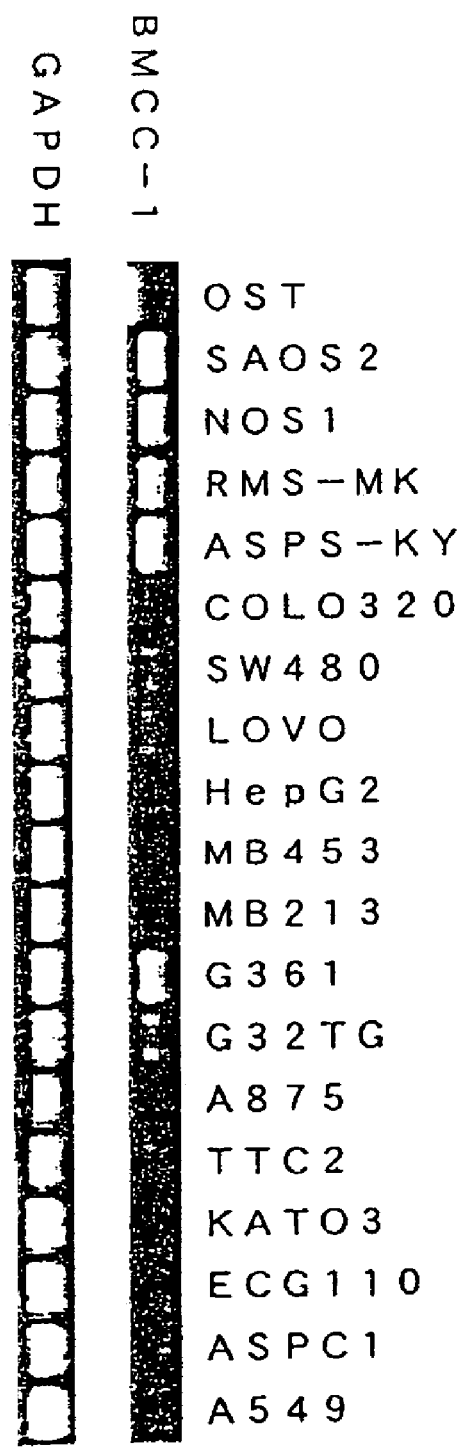
FIG. 4 is a figure corresponding to an electropherogram showing the results of determination of the expression levels of the BMCC1 gene in human cancer cell lines by semi-quantitative PCR.

Example 12) Determination of Gene Expression Levels that are Dependent on Cancer Cell Lines by Semi-Quantitative PCR RT-PCR was performed on the total RNAs of human cancer cell lines obtained in Example 2 under the conditions described in Example 9. These reaction solutions were electrophoresed on 2.5% agarose gel. The results confirmed that the distribution of the BMCC1 gene expression was tissue-specific among the cancer cell lines. Results are shown in FIG. 4.

Figure 5:
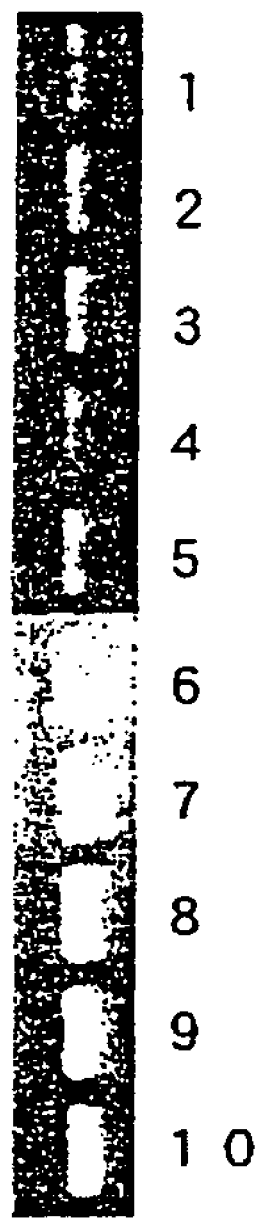
FIG. 5 is a figure corresponding to an electropherogram showing the results of determination of the expression levels of the BMCC1 gene in differentiated states of HeLa cell by semi-quantitative PCR.

Example 13) Determination of Gene Expression Levels that are Dependent on Cell Differentiation by Semi-Quantitative PCR The reagent that was commonly used to induce the differentiation and apoptosis of nerve cells (retinoic acid) was employed in the experiments as described below. CHP134 cells were inoculated in a 10 cm-diameter dish at a cell number of $1\times10^6$ and cultured in a serum-free medium to which 100 ng/ml of GDNF and retinoic acid (Sigma) (to finally be 5 µM) had been added. After incubation for 7 days, the total RNA was extracted from the cells under the conditions described in Example 2 and RT-PCR was performed under the conditions described in Example 9. These reaction solutions were electrophoresed on 2.5% agarose gel. The results confirmed that the expression of the BMCC1 gene was enhanced in a differentiated cell-specific manner. Results are shown in FIG. 5.

Here, in FIG. 5 the samples in each lane are as follows:
Lane 1: untreated and the BMCC1 expression was measured
Lane 2: 5 days after addition of retinoic acid, the BMCC1 expression was measured.
Lane 3: 7 days after addition of retinoic acid, the BMCC1 expression was measured.
Lane 4: 5 days after addition of retinoic acid and GDNF, the BMCC1 expression was measured.
Lane 5: 7 days after addition of retinoic acid and GDNF, the BMCC1 expression was measured.
Lane 6: untreated and the GAPDH expression was measured
Lane 7: 5 days after addition of retinoic acid, the GAPDH expression was measured.
Lane 8: 7 days after addition of retinoic acid, the GAPDH expression was measured.
Lane 9: 5 days after addition of retinoic acid and GDNF, the GAPDH expression was measured.
Lane 10: 7 days after addition of retinoic acid and GDNF, the GAPDH expression was measured.

Example 14) Determination of Gene Expression Levels that are Dependent on Cell Cycle Phases by Semi-Quantitative PCR PCR primers were designed based on a portion of the base sequence of the BMCC1 gene, and HeLa cells were used for comparative quantification of cell cycle phase-dependent gene expression levels. The HeLa cells used were treated in each of the following manners.
(1) Untreated
(2) Treated with 400 µM of mimosine for 18 hours, with 65% of the cells arrested in the G1 phase.
(3) Treated with 2 mM thymidine for 20 hours, with 100% of the cells arrested in the S phase.
(4) Treated with 0.6 µg/ml of nocodazole, with 85% of the cells arrested in the G2/M phase.

Figure 6:
FIG. 6 is a figure corresponding to an electropherogram showing the results of determination of the expression levels of the BMCC1 gene in different cell cycle phases of HeLa cell by semi-quantitative PCR.
Figure 7:
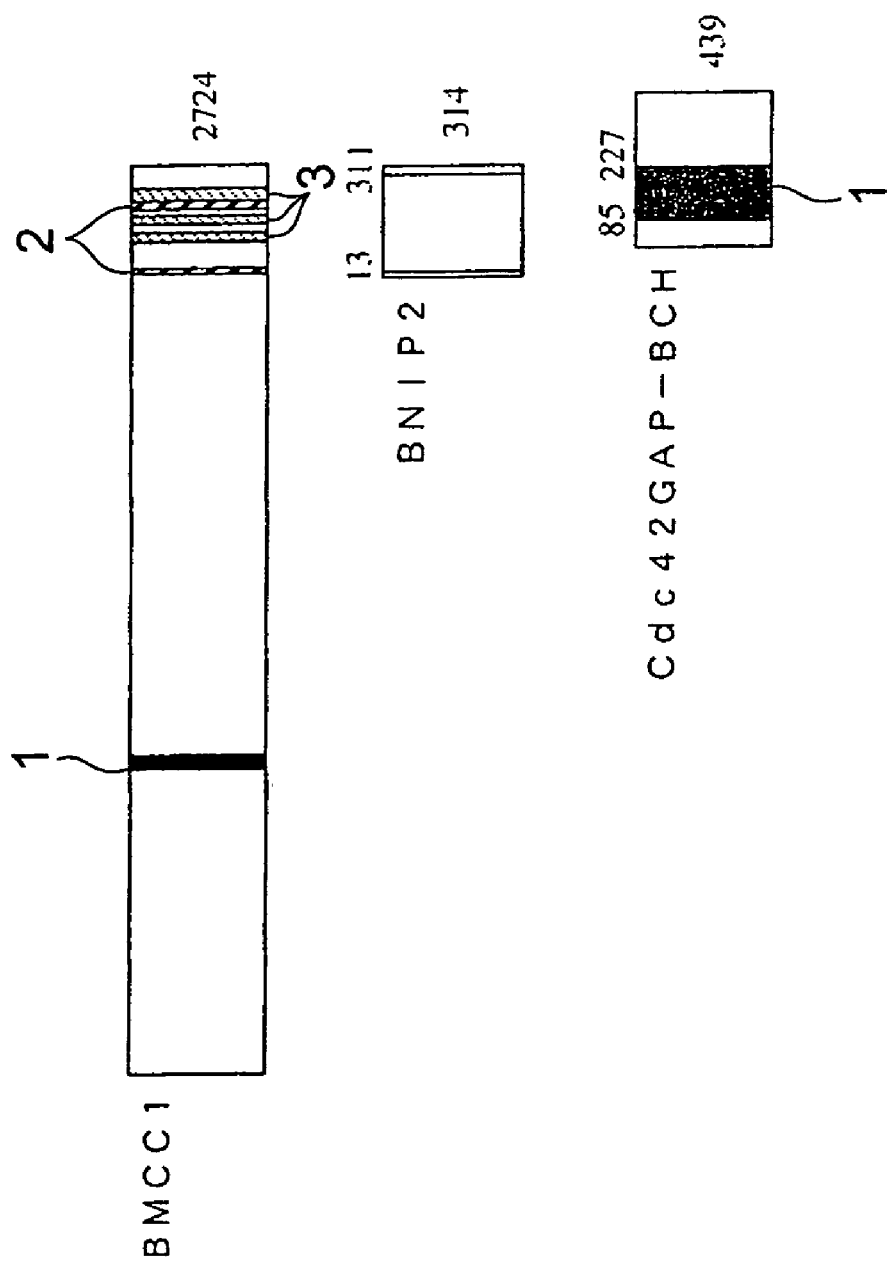
FIG. 7 is a schematic representation of the predicted domain structures of BMCC1, BNIP2 and Cdc42GAP-BCH by PSORT2.

Total mRNAs were extracted from the aforementioned 4 types of HeLa cells under the conditions described in Example 2 and RT-PCR was performed under the conditions described in Example 9. These reaction solutions were electrophoresed on 1% agarose gel. The results confirmed that the expression of the BMCC1 gene expression was specifically enhanced in the G1 phase. Results are shown in FIG. 6. Here, in FIG. 6 the samples in each lane are as follows:
Lane 1: G1 phase and the BMCC1 expression was measured.
Lane 2: S phase and the BMCC1 expression was measured.
Lane 3: G2/M phase and the BMCC1 expression was measured.
Lane 4: untreated and the BMCC1 expression was measured.
Lane 5: G1 phase and the GAPDH was measured.
Lane 6: S1 phase; and the GAPDH was measured.
Lane 7: G2/M phase; and the GAPDH was measured.
Lane 8: untreated; and the GAPDH was measured.

Example 15) Determination of Gene Expression Levels that are Dependent on Neuroblastoma Clinical Tissues by Quantitative Real Time PCR (Classification of Neuroblastoma Clinical Tissues)
Clinical tissues of neuroblastoma were classified according to the following items:
Age of onset: less than one year (Group 1); older than one year (Group 2)
Stage: 1, 2 or 4s (Group 1); 3 or 4 (Group 2)
Mass screening: positive (Group 1); negative (Group 2)
Amplification of MYCN: no amplification (Group 1); amplification (Group 2)
Expression of TrkA: high expression (Group 1); low expression (Group 2)
Onset site: other than adrenal gland (Group 1); adrenal gland (Group 2)
Prognosis: survived (Group 1); died (Group 2)
It is recognized that in each item Group 1 is an index of favorable prognosis and Group 2 is an index of unfavorable prognosis.

The expression levels of the human BMCC1 gene in the classified clinical specimens were determined by quantitative real time RT-PCR.

(Reverse Transcription (RT))
The total RNA (15 µg) of a clinical tissue of neuroblastoma was reverse-transcribed into cDNA using a Superscript. II reverse transcriptase (GIBCO).

(PCR)
PCR was performed on 7700Prism (Perkin-Elmer). cDNA (2 µl), primers (final concentration of 300 nM), probe (final concentration of 208 nM), 2.5 µl of 1×TaqMan Universal PCR Master Mix (Perkin-Elmer) were combined to make 25 µl with sterile distilled water. After allowing this mixed solution to stand at 50° C. for 2 minutes and further denaturing it at 95° C. for 10 minutes, a cycle of 95° C. for 15 seconds and 60° C. for one minute was repeated 40 times to perform PCR. For the primers and the probe of human BMCC1 gene, the oligonucleotides having the base sequences described below were used.

```
FW:
5'GGACAGTGGTCATTGGAGAACA3'          (SEQ ID NO: 50)

RV:
5'TTAGACCGTCCCCATAGTATCCTC3'        (SEQ ID NO: 51)

Probe:
5'FAM-ACATGAAGGTCATCGAGCCCTACAGGAG  (SEQ ID NO: 52)
AG-TAMRA3'
```

GAPDH was used as the positive control. For the primers and the probe, the oligonucleotides having the base sequences described below were used.

```
FW:      5'GAAGGTGAAGGTCGGAGTC3'      (SEQ ID NO: 53)

RV:      5'GAAGATGGTGATGGGATTTC3'     (SEQ ID NO: 54)

Probe:   5'CAAGCTTCCCGTTCTCAGCC3'     (SEQ ID NO: 55)
```

The quantification of BMCC1 was conducted by calculation based on comparison between plasmids containing BMCC1 whose concentration had been previously measured and GAPDH. In every case BMCC1 displayed high expression in Group 1. Results are shown in Table 1.

TABLE 1

| | Number of patients | Expression level of BMCC1 Mean ± SEM | p value |
|---|---|---|---|
| age of onset | | | |
| less than one year | 63 | 1.823 ± 0.23 | 0.0003 |
| older than one year | 36 | 0.633 ± 0.146 | |
| stage | | | |
| 1, 2, or 4s | 59 | 1.965 ± 0.232 | <.0001 |
| 3 or 4 | 40 | 0.542 ± 0.131 | |
| mass screening | | | |
| positive | 55 | 1.875 ± 0.217 | 0.0007 |
| negative | 44 | 0.784 ± 0.220 | |
| amplification of MYCN | | | |
| no | 70 | 1.796 ± 0.205 | <.0001 |
| yes | 28 | 0.296 ± 0.098 | |
| expression of TrkA | | | |
| high expression | 54 | 1.814 ± 0.221 | 0.004 |
| low expression | 45 | 0.882 ± 0.223 | |

TABLE 1-continued

| | Number of patients | Expression level of BMCC1 Mean ± SEM | p value |
|---|---|---|---|
| lesion | | | |
| other than adrenal gland | 37 | 1.862 ± 0.299 | 0.0306 |
| adrenal gland | 60 | 1.124 ± 0.189 | |
| prognosis | | | |
| survival | 77 | 1.632 ± 0.195 | 0.007 |
| death | 21 | 0.560 ± 0.199 | |

Example 16) Structural Analysis of BMCC1 Protein

The structure of the BMCC1 protein was analyzed using PSORT II (Nakai K. et al: Trends Biochem Sci. 24 (1): 34–36 (1999)), SOPM (Geourjon C et al., Eng. 7(2): 157–164 (1994)) and TM pred (Geourjon C et al., Eng. 7(2): 157–164 (1994)). FIG. 1 shows a schematic representation of the structure of the BMCC1 protein that was deduced from the results obtained. In the figure, the band part (1) blacked represents a coiled coil region (No. 917 residue to No. 946 residue), the hatched band part (2) represents a nucleus translocation signal region (Region 1: No. 2434 residue to No. 2441 residue; Region 2: No. 2604 residue to No. 2608 residue) and the hatched band part (3) represents a transmembrane region Region 1: No. 7967 residue to No. 8010 residue; Region 2: No. 8215 residue to No. 8291 residue).

INDUSTRIAL APPLICABILITY

As described above, by utilizing the human BMCC1 gene and protein according to this invention, the invention discloses base sequences relating to favorable or unfavorable prognosis of neuroblastoma and will enable the provision of their genetic information and the function of the protein that is a transcript of said gene.

The invention claimed is:

1. An isolated nucleic acid encoding the protein of SEQ ID NO:1.

2. The isolated nucleic acid of SEQ ID NO:2.

* * * * *

SEQUENCE LISTING

```
<160> NUMBER OF SEQ ID NOS: 55

<210> SEQ ID NO 1
<211> LENGTH: 2724
<212> TYPE: PRT
<213> ORGANISM: Homo sapiens

<400> SEQUENCE: 1

Met Val Ser Asn Ser Arg Thr Ser Thr Glu Ala Val Ala Gly Ser
  1               5                  10                  15

Ala Pro Leu Ser Gln Gly Ser Ser Gly Ile Met Glu Leu Tyr Gly Ser
                 20                  25                  30

Asp Ile Glu Pro Gln Pro Ser Ser Val Asn Phe Ile Glu Asn Pro Pro
             35                  40                  45

Asp Leu Asn Asp Ser Asn Gln Ala Gln Val Asp Ala Asn Val Asp Leu
         50                  55                  60
```

-continued

```
Val Ser Pro Asp Ser Gly Leu Ala Thr Ile Arg Ser Arg Ser Ser
 65              70                  75                  80

Lys Glu Ser Ser Val Phe Leu Ser Asp Asp Ser Pro Val Gly Glu Gly
                 85                  90                  95

Ala Gly Pro His His Thr Leu Leu Pro Gly Leu Asp Ser Tyr Ser Pro
                100                 105                 110

Ile Pro Glu Gly Ala Val Ala Glu His Ala Trp Ser Gly Glu His
            115                 120                 125

Gly Glu His Phe Asp Leu Phe Asn Phe Asp Pro Ala Pro Met Ala Ser
        130                 135                 140

Gly Gln Ser Gln Gln Ser Ser His Ser Ala Asp Tyr Ser Pro Ala Asp
145                 150                 155                 160

Asp Phe Phe Pro Asn Ser Asp Leu Ser Glu Gly Gln Leu Pro Ala Gly
                165                 170                 175

Pro Glu Gly Leu Asp Gly Met Gly Thr Asn Met Ser Asn Tyr Ser Ser
            180                 185                 190

Ser Ser Leu Leu Ser Gly Ala Gly Lys Asp Ser Leu Val Glu His Asp
        195                 200                 205

Glu Glu Phe Val Gln Arg Gln Asp Ser Pro Arg Asp Asn Ser Glu Arg
    210                 215                 220

Asn Leu Ser Leu Thr Asp Phe Val Gly Asp Glu Ser Pro Ser Pro Glu
225                 230                 235                 240

Arg Leu Lys Asn Thr Gly Lys Arg Ile Pro Pro Thr Pro Met Asn Ser
                245                 250                 255

Leu Val Glu Ser Ser Pro Ser Thr Glu Glu Pro Ala Ser Leu Tyr Thr
            260                 265                 270

Glu Asp Met Thr Gln Lys Ala Thr Asp Thr Gly His Met Gly Pro Pro
        275                 280                 285

Gln Thr His Ala Arg Cys Ser Ser Trp Trp Gly Gly Leu Glu Ile Asp
    290                 295                 300

Ser Lys Asn Ile Ala Asp Ala Trp Ser Ser Glu Gln Glu Ser Val
305                 310                 315                 320

Phe Gln Ser Pro Glu Ser Trp Lys Glu His Lys Pro Ser Ser Ile Asp
                325                 330                 335

Arg Arg Ala Ser Asp Ser Val Phe Gln Pro Lys Ser Leu Glu Phe Thr
            340                 345                 350

Lys Ser Gly Pro Trp Glu Ser Glu Phe Gly Gln Pro Glu Leu Gly Ser
        355                 360                 365

Asn Asp Ile Gln Asp Lys Asn Glu Glu Ser Leu Pro Phe Gln Asn Leu
    370                 375                 380

Pro Met Glu Lys Ser Pro Leu Pro Asn Thr Ser Pro Gln Gly Thr Asn
385                 390                 395                 400

His Leu Ile Glu Asp Phe Ala Ser Leu Trp His Ser Gly Arg Ser Pro
                405                 410                 415

Thr Ala Met Pro Glu Pro Trp Gly Asn Pro Thr Asp Asp Gly Glu Pro
            420                 425                 430

Ala Ala Val Ala Pro Phe Pro Ala Trp Ser Ala Phe Gly Lys Glu Asp
        435                 440                 445

His Asp Glu Ala Leu Lys Asn Thr Trp Asn Leu His Pro Thr Ser Ser
    450                 455                 460

Lys Thr Pro Ser Val Arg Asp Pro Asn Glu Trp Ala Met Ala Lys Ser
465                 470                 475                 480

Gly Phe Ala Phe Ser Ser Ser Glu Leu Leu Asp Asn Ser Pro Ser Glu
```

-continued

```
                485                 490                 495
Ile Asn Asn Glu Ala Ala Pro Glu Ile Trp Gly Lys Lys Asn Asn Asp
                500                 505                 510
Ser Arg Asp His Ile Phe Ala Pro Gly Asn Pro Ser Ser Asp Leu Asp
                515                 520                 525
His Thr Trp Thr Asn Ser Lys Pro Pro Lys Glu Asp Gln Asn Gly Leu
            530                 535                 540
Val Asp Pro Lys Thr Arg Gly Lys Val Tyr Glu Lys Val Asp Ser Trp
545                 550                 555                 560
Asn Leu Phe Glu Glu Asn Met Lys Lys Gly Gly Ser Asp Val Leu Val
                565                 570                 575
Pro Trp Glu Asp Ser Phe Leu Ser Tyr Lys Cys Ser Asp Tyr Ser Ala
                580                 585                 590
Ser Asn Leu Gly Glu Asp Ser Val Pro Ser Pro Leu Asp Thr Asn Tyr
            595                 600                 605
Ser Thr Ser Asp Ser Tyr Thr Ser Pro Thr Phe Ala Gly Asp Glu Lys
            610                 615                 620
Glu Thr Glu His Lys Pro Phe Ala Lys Glu Glu Gly Phe Glu Ser Lys
625                 630                 635                 640
Asp Gly Asn Ser Thr Ala Glu Glu Thr Asp Ile Pro Pro Gln Ser Leu
                645                 650                 655
Gln Gln Ser Ser Arg Asn Arg Ile Ser Ser Gly Pro Gly Asn Leu Asp
                660                 665                 670
Met Trp Ala Ser Pro His Thr Asp Asn Ser Ser Glu Ile Asn Thr Thr
            675                 680                 685
His Asn Leu Asp Glu Asn Glu Leu Lys Thr Glu His Thr Asp Gly Lys
            690                 695                 700
Asn Ile Ser Met Glu Asp Asp Val Gly Glu Ser Ser Gln Ser Ser Tyr
705                 710                 715                 720
Asp Asp Pro Ser Met Met Gln Leu Tyr Asn Glu Thr Asn Arg Gln Leu
                725                 730                 735
Thr Leu Leu His Ser Ser Thr Asn Ser Arg Gln Thr Ala Pro Asp Ser
            740                 745                 750
Leu Asp Leu Trp Asn Arg Val Ile Leu Glu Asp Thr Gln Ser Thr Ala
            755                 760                 765
Thr Ile Ser Asp Met Asp Asn Asp Leu Asp Trp Asp Asp Cys Ser Gly
            770                 775                 780
Gly Ala Ala Ile Pro Ser Asp Gly Gln Thr Glu Gly Tyr Met Ala Glu
785                 790                 795                 800
Gly Ser Glu Pro Glu Thr Arg Phe Thr Val Arg Gln Leu Glu Pro Trp
                805                 810                 815
Gly Leu Glu Tyr Gln Glu Ala Asn Gln Val Asp Trp Glu Leu Pro Ala
            820                 825                 830
Ser Asp Glu His Thr Lys Asp Ser Ala Pro Ser Glu His His Thr Leu
            835                 840                 845
Asn Glu Lys Ser Gly Gln Leu Ile Ala Asn Ser Ile Trp Asp Ser Val
850                 855                 860
Met Arg Asp Lys Asp Met Ser Ser Phe Met Leu Pro Gly Ser Ser His
865                 870                 875                 880
Ile Thr Asp Ser Glu Gln Arg Glu Leu Pro Pro Glu Ile Pro Ser His
                885                 890                 895
Ser Ala Asn Val Lys Asp Thr His Ser Pro Asp Ala Pro Ala Ala Ser
            900                 905                 910
```

-continued

Gly Thr Ser Glu Ser Glu Ala Leu Ile Ser His Leu Asp Lys Gln Asp
            915                 920                 925

Thr Glu Arg Glu Thr Leu Gln Ser Asp Ala Ala Ser Leu Ala Thr Arg
        930                 935                 940

Leu Glu Asn Pro Gly Tyr Phe Pro His Pro Asp Pro Trp Lys Gly His
945                 950                 955                 960

Gly Asp Gly Gln Ser Glu Ser Lys Glu Ala Gln Gly Ala Thr Asp
            965                 970                 975

Arg Gly His Leu Asp Glu Glu Val Ile Ala Ser Gly Val Glu Asn
        980                 985                 990

Ala Ser Gly Ile Ser Glu Lys Gly Gln Ser Asp Gln Glu Leu Ser Ser
            995                 1000                1005

Leu Val Ala Ser Glu His Gln Glu Ile Cys Ile Lys Ser Gly Lys Ile
    1010                1015                1020

Ser Ser Leu Ala Val Thr Phe Ser Pro Gln Thr Glu Glu Pro Glu Glu
1025                1030                1035                1040

Val Leu Glu Tyr Glu Glu Gly Ser Tyr Asn Leu Asp Ser Arg Asp Val
            1045                1050                1055

Gln Thr Gly Met Ser Ala Asp Asn Leu Gln Pro Lys Asp Thr His Glu
            1060                1065                1070

Lys His Leu Met Ser Gln Arg Asn Ser Gly Glu Thr Thr Glu Thr Ser
        1075                1080                1085

Asp Gly Met Asn Phe Thr Lys Tyr Val Ser Val Pro Glu Lys Asp Leu
        1090                1095                1100

Glu Lys Thr Glu Glu Cys Asn Phe Leu Glu Pro Glu Asn Val Gly Gly
1105                1110                1115                1120

Gly Pro Pro His Arg Val Pro Arg Ser Leu Asp Phe Gly Asp Val Pro
            1125                1130                1135

Ile Asp Ser Asp Val His Val Ser Ser Thr Cys Ser Glu Ile Thr Lys
            1140                1145                1150

Asn Leu Asp Val Lys Gly Ser Glu Asn Ser Leu Pro Gly Ala Gly Ser
            1155                1160                1165

Ser Gly Asn Phe Asp Arg Asp Thr Ile Ser Ser Glu Tyr Thr His Ser
    1170                1175                1180

Ser Ala Ser Ser Pro Glu Leu Asn Asp Ser Ser Val Ala Leu Ser Ser
1185                1190                1195                1200

Trp Gly Gln Gln Pro Ser Ser Gly Tyr Gln Glu Glu Asn Gln Gly Asn
            1205                1210                1215

Trp Ser Glu Gln Asn His Gln Glu Ser Glu Leu Ile Thr Thr Asp Gly
            1220                1225                1230

Gln Val Glu Ile Val Thr Lys Val Lys Asp Leu Glu Lys Asn Arg Ile
        1235                1240                1245

Asn Glu Phe Glu Lys Ser Phe Asp Arg Lys Thr Pro Thr Phe Leu Glu
        1250                1255                1260

Ile Trp Asn Asp Ser Val Asp Gly Asp Ser Phe Ser Ser Leu Ser Ser
1265                1270                1275                1280

Pro Glu Thr Gly Lys Tyr Ser Glu His Ser Gly Thr His Gln Glu Ser
            1285                1290                1295

Asn Leu Ile Ala Ser Tyr Gln Glu Lys Asn Glu His Asp Ile Ser Ala
        1300                1305                1310

Thr Val Gln Ser Glu Asp Ala Arg Val Ile Ser Thr Ser Ser Gly Ser
        1315                1320                1325

```
Asp Asp Asp Ser Val Gly Gly Glu Glu Ser Ile Glu Glu Ile Gln
        1330                1335                1340
Val Ala Asn Cys His Val Ala Glu Asp Glu Ser Arg Ala Trp Asp Ser
1345                1350                1355                1360
Leu Asn Glu Ser Asn Lys Phe Leu Val Thr Ala Asp Pro Lys Ser Glu
                1365                1370                1375
Asn Ile Tyr Asp Tyr Leu Asp Ser Ser Glu Pro Ala Glu Asn Glu Asn
            1380                1385                1390
Lys Ser Asn Pro Phe Cys Asp Asn Gln Gln Ser Ser Pro Asp Pro Trp
        1395                1400                1405
Thr Phe Ser Pro Leu Thr Glu Thr Glu Met Gln Ile Thr Ala Val Glu
    1410                1415                1420
Lys Glu Lys Arg Ser Ser Pro Glu Thr Gly Thr Thr Gly Asp Val Ala
1425                1430                1435                1440
Trp Gln Ile Ser Pro Lys Ala Ser Phe Pro Lys Asn Glu Asp Asn Ser
                1445                1450                1455
Gln Leu Glu Met Leu Gly Phe Ser Ala Asp Ser Thr Glu Trp Trp Lys
            1460                1465                1470
Ala Ser Pro Gln Glu Gly Arg Leu Ile Glu Ser Pro Phe Glu Arg Glu
        1475                1480                1485
Leu Ser Asp Ser Ser Gly Val Leu Glu Ile Asn Ser Ser Val His Gln
    1490                1495                1500
Asn Ala Ser Pro Trp Gly Val Pro Val Gln Gly Asp Ile Glu Pro Val
1505                1510                1515                1520
Glu Thr His Tyr Thr Asn Pro Phe Ser Asp Asn His Gln Ser Pro Phe
                1525                1530                1535
Leu Glu Gly Asn Gly Lys Asn Ser His Glu Gln Leu Trp Asn Ile Gln
            1540                1545                1550
Pro Arg Gln Pro Asp Pro Asp Ala Asp Lys Phe Ser Gln Leu Val Lys
        1555                1560                1565
Leu Asp Gln Ile Lys Glu Lys Asp Ser Arg Glu Gln Thr Phe Val Ser
    1570                1575                1580
Ala Ala Gly Asp Glu Leu Thr Pro Glu Thr Pro Thr Gln Glu Gln Cys
1585                1590                1595                1600
Gln Asp Thr Met Leu Pro Val Cys Asp His Pro Asp Thr Ala Phe Thr
                1605                1610                1615
His Ala Glu Glu Asn Ser Cys Val Thr Ser Asn Val Ser Thr Asn Glu
            1620                1625                1630
Gly Gln Glu Thr Asn Gln Trp Glu Gln Glu Lys Ser Tyr Leu Gly Glu
        1635                1640                1645
Met Thr Asn Ser Ser Ile Ala Thr Glu Asn Phe Pro Ala Val Ser Ser
    1650                1655                1660
Pro Thr Gln Leu Ile Met Lys Pro Gly Ser Glu Trp Asp Gly Ser Thr
1665                1670                1675                1680
Pro Ser Glu Asp Ser Arg Gly Thr Phe Val Pro Asp Ile Leu His Gly
                1685                1690                1695
Asn Phe Gln Glu Gly Gly Gln Leu Ala Ser Ala Ala Pro Asp Leu Trp
            1700                1705                1710
Ile Asp Ala Lys Lys Pro Phe Ser Leu Lys Ala Asp Gly Glu Asn Pro
        1715                1720                1725
Asp Ile Leu Thr His Cys Glu His Asp Ser Asn Ser Gln Ala Ser Asp
    1730                1735                1740
Ser Pro Asp Ile Cys His Asp Ser Glu Ala Lys Gln Glu Thr Glu Lys
```

-continued

```
              1745                1750                1755                1760
His Leu Ser Ala Cys Met Gly Pro Glu Val Glu Ser Glu Leu Cys
                    1765                1770                1775
Leu Thr Glu Pro Glu Ile Asp Glu Pro Ile Tyr Glu Pro Gly Arg
                    1780                1785                1790
Glu Phe Val Pro Ser Asn Ala Glu Leu Asp Ser Glu Asn Ala Thr Val
                    1795                1800                1805
Leu Pro Pro Ile Gly Tyr Gln Ala Asp Ile Lys Gly Ser Ser Gln Pro
                    1810                1815                1820
Ala Ser His Lys Gly Ser Pro Glu Pro Ser Glu Ile Asn Gly Asp Asn
1825                1830                1835                1840
Ser Thr Gly Leu Gln Val Ser Glu Lys Gly Ala Ser Pro Asp Met Ala
                    1845                1850                1855
Pro Ile Leu Glu Pro Val Asp Arg Arg Ile Pro Arg Ile Glu Asn Val
                    1860                1865                1870
Ala Thr Ser Ile Phe Val Thr His Gln Glu Pro Thr Pro Glu Gly Asp
                    1875                1880                1885
Gly Ser Trp Ile Ser Asp Ser Phe Ser Pro Glu Ser Gln Pro Gly Ala
                    1890                1895                1900
Arg Ala Leu Phe Asp Gly Asp Pro His Leu Ser Thr Glu Asn Pro Ala
1905                1910                1915                1920
Leu Val Pro Asp Ala Leu Leu Ala Ser Asp Thr Cys Leu Asp Ile Ser
                    1925                1930                1935
Glu Ala Ala Phe Asp His Ser Phe Ser Asp Ala Ser Gly Leu Asn Thr
                    1940                1945                1950
Ser Thr Gly Thr Ile Asp Asp Met Ser Lys Leu Thr Leu Ser Glu Gly
                    1955                1960                1965
His Pro Glu Thr Pro Val Asp Gly Asp Leu Gly Lys Gln Asp Ile Cys
                    1970                1975                1980
Ser Ser Glu Ala Ser Trp Gly Asp Phe Glu Tyr Asp Val Met Gly Gln
1985                1990                1995                2000
Asn Ile Asp Glu Asp Leu Leu Arg Glu Pro Glu His Phe Leu Tyr Gly
                    2005                2010                2015
Gly Asp Pro Pro Leu Glu Glu Asp Ser Leu Lys Gln Ser Leu Ala Pro
                    2020                2025                2030
Tyr Thr Pro Pro Phe Asp Leu Ser Tyr Leu Thr Glu Pro Ala Gln Ser
                    2035                2040                2045
Ala Glu Thr Ile Glu Glu Ala Gly Ser Pro Glu Asp Glu Ser Leu Gly
                    2050                2055                2060
Cys Arg Ala Ala Glu Ile Val Leu Ser Ala Leu Pro Asp Arg Arg Ser
2065                2070                2075                2080
Glu Gly Asn Gln Ala Glu Thr Lys Asn Arg Leu Pro Gly Ser Gln Leu
                    2085                2090                2095
Ala Val Leu His Ile Arg Glu Asp Pro Glu Ser Val Tyr Leu Pro Val
                    2100                2105                2110
Gly Ala Gly Ser Asn Ile Leu Ser Pro Ser Asn Val Asp Trp Glu Val
                    2115                2120                2125
Glu Thr Asp Asn Ser Asp Leu Pro Ala Gly Asp Ile Gly Pro Pro
                    2130                2135                2140
Asn Gly Ala Ser Lys Glu Ile Pro Glu Leu Glu Glu Lys Thr Ile
2145                2150                2155                2160
Pro Thr Lys Glu Pro Glu Gln Ile Lys Ser Glu Tyr Lys Glu Glu Arg
                    2165                2170                2175
```

-continued

Cys Thr Glu Lys Asn Glu Asp Arg His Ala Leu His Met Asp Tyr Ile
            2180                2185                2190

Leu Val Asn Arg Glu Glu Asn Ser His Ser Lys Pro Glu Thr Cys Glu
        2195                2200                2205

Glu Arg Glu Ser Ile Ala Glu Leu Glu Leu Tyr Val Gly Ser Lys Glu
    2210                2215                2220

Thr Gly Leu Gln Gly Thr Gln Leu Ala Ser Phe Pro Asp Thr Cys Gln
2225                2230                2235                2240

Pro Ala Ser Leu Asn Glu Arg Lys Gly Leu Ser Ala Glu Lys Met Ser
            2245                2250                2255

Ser Lys Gly Asp Thr Arg Ser Ser Phe Glu Ser Pro Ala Gln Asp Gln
        2260                2265                2270

Ser Trp Met Phe Leu Gly His Ser Glu Val Gly Asp Pro Ser Leu Asp
    2275                2280                2285

Ala Arg Asp Ser Gly Pro Gly Trp Ser Gly Lys Thr Val Glu Pro Phe
        2290                2295                2300

Ser Glu Leu Gly Leu Gly Glu Gly Pro Gln Leu Gln Ile Leu Glu Glu
2305                2310                2315                2320

Met Lys Pro Leu Glu Ser Leu Ala Leu Glu Glu Ala Ser Gly Pro Val
            2325                2330                2335

Ser Gln Ser Gln Lys Ser Lys Ser Arg Gly Arg Ala Gly Pro Asp Ala
        2340                2345                2350

Val Thr His Asp Ser Glu Trp Glu Met Leu Ser Pro Gln Pro Val Gln
    2355                2360                2365

Lys Asn Met Ile Ser Asp Thr Glu Met Glu Glu Thr Glu Phe Leu
    2370                2375                2380

Glu Leu Gly Thr Arg Ile Ser Arg Pro Asn Gly Leu Leu Ser Glu Asp
2385                2390                2395                2400

Val Gly Met Asp Ile Pro Phe Glu Glu Gly Val Leu Ser Pro Ser Ala
            2405                2410                2415

Ala Asp Met Arg Pro Glu Pro Pro Asn Ser Leu Asp Leu Asn Asp Thr
        2420                2425                2430

His Pro Arg Arg Ile Lys Leu Thr Ala Pro Asn Ile Asn Leu Ser Leu
    2435                2440                2445

Asp Gln Ser Glu Gly Ser Ile Leu Ser Asp Asp Asn Leu Asp Ser Pro
        2450                2455                2460

Asp Glu Ile Asp Ile Asn Val Asp Glu Leu Asp Thr Pro Asp Glu Ala
2465                2470                2475                2480

Asp Ser Phe Glu Tyr Thr Gly His Asp Pro Thr Ala Asn Lys Asp Ser
            2485                2490                2495

Gly Gln Glu Ser Glu Ser Ile Pro Glu Tyr Thr Ala Glu Glu Glu Arg
        2500                2505                2510

Glu Asp Asn Arg Leu Trp Arg Thr Val Val Ile Gly Glu Gln Glu Gln
    2515                2520                2525

Arg Ile Asp Met Lys Val Ile Glu Pro Tyr Arg Arg Val Ile Ser His
    2530                2535                2540

Gly Gly Tyr Tyr Gly Asp Gly Leu Asn Ala Ile Ile Val Phe Ala Ala
2545                2550                2555                2560

Cys Phe Leu Pro Asp Ser Ser Arg Ala Asp Tyr His Tyr Val Met Glu
            2565                2570                2575

Asn Leu Phe Leu Tyr Val Ile Ser Thr Leu Glu Leu Met Val Ala Glu
        2580                2585                2590

-continued

Asp Tyr Met Ile Val Tyr Leu Asn Gly Ala Thr Pro Arg Arg Arg Met
        2595                2600                2605

Pro Gly Leu Gly Trp Met Lys Lys Cys Tyr Gln Met Ile Asp Arg Arg
    2610                2615                2620

Leu Arg Lys Asn Leu Lys Ser Phe Ile Val His Pro Ser Trp Phe
2625                2630                2635                2640

Ile Arg Thr Ile Leu Ala Val Thr Arg Pro Phe Ile Ser Ser Lys Phe
        2645                2650                2655

Ser Ser Lys Ile Lys Tyr Val Asn Ser Leu Ser Glu Leu Ser Gly Leu
            2660                2665                2670

Ile Pro Met Asp Cys Ile His Ile Pro Glu Ser Ile Ile Lys Leu Asp
        2675                2680                2685

Glu Glu Leu Arg Glu Ala Ser Glu Ala Ala Lys Thr Ser Cys Leu Tyr
    2690                2695                2700

Asn Asp Pro Glu Met Ser Ser Met Glu Lys Asp Ile Asp Leu Lys Leu
2705                2710                2715                2720

Lys Glu Lys Pro

<210> SEQ ID NO 2
<211> LENGTH: 11690
<212> TYPE: DNA
<213> ORGANISM: Homo sapiens

<400> SEQUENCE: 2

```
gaattgtcta tttcacagca atattaccag tgacttgaaa gcatttacag acaagtttgg      60
ttttgatgtc ctcatcctgt tctccagcta tctgtcagag gagcagcagc cgagacgaca     120
gattgctgtg tactcagaaa acatggagct gtgcagtcag atttgctgtg agctggaaga     180
gtgtcagaac ccttgcctag aactggagcc ctttgactgt ggctgtgatg agatcctggt     240
gtaccaacaa gaggacccttt cagtgacttg tgatcaggtg gttctcgttg tcaaggaagt     300
catcaacagg aggtgtccag agatggtctc caatagccgg acatcctcaa cagaagccgt     360
ggcaggcagt gcccccctct cccagggggtc ttctgggatt atggaattgt atggttctga    420
catagagcca caacccagct ctgtgaattt catagagaac cctccagatc tcaatgattc     480
taaccaggct caggtggatg ccaatgtaga ccttgttagc ccagacagcg gactggctac     540
cattaggagc agccgctcat ccaaggagag ctctgttttc ctcagtgacg acagcccccgt    600
gggagaaggt gctgggcctc accacaccct tctcccaggg cttgactcct acagcccccat    660
ccctgaaggg gcggtggcgg aggaacatgc atggtctgga gaacacggtg agcacttcga     720
cctcttcaat tttgacccag cacccatggc ttctgggcag tcccagcaat cttctcattc     780
tgcagactac tcccccagcag atgacttctt ccccaacagt gacctgtcag aaggacagct    840
ccccgctggg cctgaaggac ttgatggcat gggaaccaac atgtctaatt attcatccag     900
ttcacttttg tcaggggctg gcaaagatag ccttgtggaa catgatgagg agtttgtcca     960
gagacaagac agtccagag ataactctga agaaatttg agcctgacag attttgtggg     1020
agatgaatcc ccttccccag aaaggctaaa aaatactgga aagaggatcc caccaacacc    1080
catgaatagt ttagtagaaa gctcgccatc cactgaagaa ccagcctcac tctatacaga    1140
agatatgacc caaaaagcaa ctgacacagg tcacatgggg ccacctcaga cccatgcacg    1200
gtgcagcagc tggtggggtg gtttggaaat tgactccaaa aatattgcag atgcgtggag    1260
ttccagtgaa caggaatctg ttttccagag ccctgaatca tggaaagagc ataagccaag    1320
ctccattgat aggagagcct cagattctgt atttcaacca aagagcctcg aatttacaaa    1380
```

-continued

```
gtcaggtccc tgggagtctg aatttggtca gcctgaactg ggtagcaatg atattcaaga      1440
caaaaatgag gaaagcttgc cgttccagaa cctgcccatg gagaagtcac ctttgccaaa      1500
tacatctccc caaggaacaa accacctgat agaagacttt gcttctttgt ggcattctgg      1560
tcgctctccc acagccatgc ccgagccctg gggaaatcct acagatgatg gtgaaccagc      1620
agctgtggcg ccattcccag cctggagtgc atttggtaaa aagatcatg atgaagcttt       1680 aaaaaatacc tggaatttgc acccaacaag cagcaagaca ccttctgtta gggacccgaa      1740
tgagtgggcc atggcaaaaa gtgggtttgc cttttcttct tcagaactac tggacaattc      1800
acccagtgag ataaacaatg aagcagctcc agaaatctgg ggcaagaaaa acaatgactc      1860
cagggatcac atctttgcac ctggaaatcc cagttctgat ctggatcaca catggactaa      1920
ttctaagcca ccaaaagaag atcagaatgg tttagtggat cctaaaacta ggggcaaggt      1980
atatgaaaag gtagattcct ggaaccttt tgaggagaat atgaagaaag gagggtcaga      2040
tgtcctagtt ccttgggaag attccttctt atcttacaaa tgttctgatt acagtgcatc      2100
caacctagga gaagattcgg tgccttcccc cttagatacc aattattcca cctcagactc      2160
ttacacatca ccaacatttg ctggagacga aaaggaaact gaacacaagc catttgctaa      2220
agaggaaggt tttgagtcaa agatggtaa ctccacggca gagggactg acattcctcc       2280 tcagtcactg caacagtcat ctcgaaatcg aatcagttca ggtcctggga acctagacat      2340
gtgggcttca cctcatacag ataacagttc tgaaataaat accactcaca acctggatga      2400
aaatgaactc aagacagagc acacagatgg taagaatatc tccatggagg atgacgtcgg      2460
ggaaagcagc cagtccagtt acgacgaccc cagcatgatg caactgtaca atgaaacaaa      2520
ccgacaactc acactttgc acagcagcac caactcccgg cagacggccc ctgacagtct       2580
cgacttgtgg aacagagtga ttttggagga tactcagtcc actgcaacga tctcagatat      2640
ggacaatgat ttggactggg atgactgcag tgggggtgcg gcaatcccca gtgatggtca      2700
aacagaagga tacatggctg aaggttccga gccggaaacc cgatttacag tgagacagct      2760
ggaaccctgg ggcttggagt atcaggaagc aaatcaggta gattgggagc tccctgcctc      2820
tgatgagcat accaaggaca gtgctcccag tgaacatcac acattgaatg agaaaagtgg      2880
gcagctaatt gcaaacagta tttgggattc tgtcatgaga gataaagaca tgtcatcatt      2940
catgttacca ggctcctcac atatcacaga ttcagagcaa agggaattgc ctcctgaaat      3000 cccccagccat tcagcaaatg ttaaagacac tcattcccca gatgcgccag cagcctctgg      3060
aaccagtgaa tcagaggcac ttatatctca tcttgacaag caggacacag agagggaaac      3120
cctgcaaagt gatgcagcat ccttggcgac taggcttgag aatccagggt attttccaca      3180
cccagatcca tggaaaggtc atggcgatgg acaaagtgaa agtgagaagg aagcccaggg      3240
agccactgac agggggcacc ttgatgaaga ggaggtgatc gcctctggtg tggagaatgc      3300
ctcagggatt tctgaaaaag gcagagtga ccaggaactg tcttctctgg ttgcatctga       3360
acatcaggaa atctgcatta aatcaggcaa aatcagctct cttgctgtca ctttcagtcc      3420
tcaaaccgag gaaccagagg aagttttaga gtatgaggag gggtcttaca atctagactc      3480
ccgtgatgtg caaacaggga tgtccgcaga taacctgcag ccaaaagata cccatgaaaa      3540
acacctcatg agtcaaagaa attcaggtga aactactgag acttcagatg ggatgaattt      3600
cacaaaatat gtatctgtac ctgaaaagga tcttgagaaa actgaagaat gtaacttttct     3660 agagccagag aacgtgggtg gagggccacc tcacagagtt ccccgaagtc ttgattttgg      3720
```

```
ggacgtccct atagacagtg atgtgcatgt cagcagcaca tgttctgaga taaccaaaaa    3780
tcttgacgtt aagggggtctg aaaatagcct tccaggagcc ggttcgtctg gaaattttga    3840
cagagatact atttctagtg agtatactca ttcaagtgca tcaagtcctg agttaaatga    3900
ctcttcagtt gcactgtcct cctggggcca gcaacccagt tctgggtatc aagaagaaaa    3960
ccaaggcaac tggagtgaac agaatcacca agaatctgaa ctaattacca ctgatggcca    4020
agtagaaata gttaccaaag tgaaggattt agagaaaaac agaataaatg agtttgaaaa    4080
gagctttgat cgcaaaactc ctacattttt agagatctgg aatgactcag ttgatggtga    4140 ttcctttttcc tctttatcca gtcctgaaac aggcaaatat tctgaacatt cagggacaca    4200
tcaggaaagc aatctaattg ctagctacca ggagaaaaat gaacatgaca tttctgcaac    4260
tgtgcaatca gaggatgcca gggtcatttc aacaagctca ggttctgatg atgacagtgt    4320
cggtggtgaa gagtcaatag aggaagagat ccaggtggcc aactgccacg ttgctgagga    4380
tgaatccaga gctgggatt cattgaatga atcaataag ttcttggtca cagctgatcc    4440
taagtctgaa atatttatg actacctaga cagctcagag ccagcagaga atgagaataa    4500
gtcaaaccca ttctgtgaca atcaacaaag cagccctgat ccctggactt tctcaccatt    4560
aacggagact gaaatgcaga ttacagcagt ggagaaggag aagagatctt ctccagaaac    4620
agggacaaca ggagatgttg catggcaaat atctcccaaa gcttcgttcc caaagaacga    4680
agataattct caactggaaa tgctgggctt tcagctgat agcactgagt ggtggaaggc    4740
ctcaccccag gaagggagac taattgaaag tccatttgaa agggagctgt ctgactccag    4800
tggtgtgttg gagataaatt cttcagtaca ccaaaatgcc agtccctggg gagtaccagt    4860
tcagggtgat attgagcccg tggaaacaca ctatactaat cctttagtg acaaccatca    4920 gtcaccctttt ctggaaggta atgggaagaa ctcccatgag caactctgga acattcaacc    4980
aaggcagcca gacccagatg ctgacaagtt cagccagctt gtaaaattag accaaattaa    5040
agaaaaggac tcaagagagc aaaccttttgt gtctgctgct ggtgatgagc tgactcctga    5100
aacacctacc caagagcagt gtcaggacac catgctgcca gtctgtgatc atccggacac    5160 agccttttact cacgcagagg aaaatagttg tgttacatct aatgtttcaa ctaatgaagg    5220
tcaagaaaca aatcagtggg aacaagaaaa atcataccta ggtgagatga caattcaag    5280 cattgccaca gaaaattttc ctgctgtcag ttctcccacc caactgataa tgaagccagg    5340
ctctgaatgg gatggctcta ccccaagtga ggactccga ggtacctttg tgccagatat    5400
tttacatggc aactttcaag agggtgggca gctggcctct gccgcgcctg acttgtggat    5460
agatgctaag aagcccttca gttttgaaagc agatggtgag aatcctgata tcctgacgca    5520
ctgcgaacat gacagcaatt tcaggcttc cgacagccct gatatatgtc acgattctga    5580
agcaaagcaa gagactgaga agcacctcag tgcttgcatg ggacctgaag tggaatccag    5640
tgagctttgt ctcactgagc cagagataga tgaagaaccc atttatgagc tggacgggaa    5700
gtttgtccca tccaatgcag aactcgattc tgaaaacgca actgtgctgc ctccaattgg    5760
ctatcaagca gacataaagg gctcctctca gcccgcctct cataaaggtt cacctgaacc    5820
ttctgaaata acggtgaca acagtacagg tttacaagta tcagaaaaag gagccagccc    5880
agatatggcc ccaattttgg aaccagttga cagaagaatc ccaaggattg aaaatgtggc    5940
aactagcatt tttgtaactc accaagagcc aactccagaa ggtgacggtt cttggatatc    6000
agacagcttt tctcctgaaa gtcagcctgg tgcaagagct ttgtttgatg gtgatccaca    6060
tttatccaca gagaatcctg ccttggttcc tgatgctttg ctagcctcag acacttgtct    6120
```

-continued

```
ggatataagc gaagctgcct ttgaccacag tttcagcgat gcctcaggtc tcaacacatc    6180
cacgggaaca atagatgaca tgagtaaact gacattatcc gaaggccatc cggaaacgcc    6240
agttgatggg gacctaggga agcaagatat ctgctcatct gaagcctcgt ggggtgattt    6300
tgaatatgat gtaatgggcc agaatatcga tgaagattta ctgagagagc ctgaacactt    6360
cctgtatggt ggtgaccctc ctttggagga agattctctg aagcagtcgc tggcaccgta    6420
cacacctccc tttgatttgt cttatctcac agaacctgcc cagagtgctg aaacaataga    6480
ggaagctggg tctccagagg atgaatctct gggatgcaga gcagcagaga tagtgctttc    6540
tgcacttcct gatcgaagaa gtgagggaaa ccaggctgag accaaaaaca gactgcctgg    6600
atcccagctg gctgtgctgc atattcgtga agaccctgag tccgtttatt tgccggtagg    6660
agcaggctcc aacattttgt ctccatcaaa cgttgactgg gaagtagaaa cagataattc    6720
tgatttacca gcaggtggag acataggacc accaaatggt gccagcaagg aaataccaga    6780
attggaagaa gaaaaaacaa ttcctaccaa agagcctgag cagataaaat cagaatacaa    6840
ggaagaaaga tgcacagaga agaatgaaga tcgtcatgca ctacacatgg attacatact    6900
tgtaaaccgt gaagaaaatt cacactcaaa gccagagacc tgtgaagaaa gagaaagcat    6960
agctgaatta gaattgtatg taggttccaa agaaacaggg ctgcagggaa ctcagttagc    7020
aagcttccca gacacatgtc agccagcctc cttaaatgaa agaaaaggtc tctctgcaga    7080
gaaaatgtct tctaaaggcg atacgagatc atcttttgaa agccctgcac aagaccagag    7140
ttggatgttc ttgggccata gtgaggttgg tgatccatca ctggatgcca gggactcagg    7200
gcctgggtgg tctggcaaga ctgtggagcc gttctctgaa ctcggcttgg gtgagggtcc    7260
ccagctgcag attctggaag aaatgaagcc tctagaatct ttagcactag aggaagcctc    7320
tggtccagtc agccaatcac agaagagtaa gagccgaggc agggctggcc cggatgcagt    7380
tacccatgac agtgaatggg aaatgctttc accacagcct gttcagaaaa acatgatctc    7440
tgacacggaa atggaggagg agacagagtt ccttgagctc ggaaccagga tatcaagacc    7500 aaaatggacta ctgtcagagg atgtaggaat ggacatcccc tttgaagagg gcgtgctgag    7560
tcccagtgct gcagacatga ggcctgaacc tcctaattct ctggatctta atgacactca    7620
tcctcggaga atcaagctca cagccccaaa tatcaatctt tctctggacc aaagtgaagg    7680
atctattctc tctgatgata acttggacag tccagatgaa attgacatca atgtggatga    7740
acttgatacc cccgatgaag cagattcttt tgagtacact ggccatgatc ccacagccaa    7800
caaagattct ggccaagagt cagagtctat tccagaatat acggccgaag aggaacggga    7860
ggacaaccgg cttggagga cagtggtcat tggagaacaa gagcagcgca ttgacatgaa    7920
ggtcatcgag ccctacagga gagtcatttc tcacggagga tactatgggg acggtctaaa    7980
tgccatcatt gtgtttgccg cctgttttct gccagacagc agtcgggcgg attaccacta    8040
tgtcatggaa aatcttttcc tatatgtaat aagtacttta gagttgatgg tagctgaaga    8100
ctatatgatt gtgtacttga atggtgcaac cccaagaagg aggatgccag ggctaggctg    8160
gatgaagaaa tgctaccaga tgattgacag acggttgagg aagaatttga aatcattcat    8220
cattgttcat ccatcttggt tcatcagaac aatccttgct gtgacacgac ctttataag    8280 ttcaaaattc agcagtaaaa ttaaatatgt caatagctta tcagaactca gtgggctgat    8340
cccaatggat tgcatccaca ttccagagag catcatcaaa ctggatgaag aactgaggga    8400
agcatcagag gcagctaaaa ctagctgcct ttacaatgat ccagaaatgt cttctatgga    8460
```

-continued

```
gaaggatatt gacttgaagc tgaaagaaaa gccttagttg gccatgctgg aagaagagga    8520
tgcttttctg gttcatggtt ctgttgaaac atatctacct gaaagagaca gggctgatgt    8580
tacctttttc cactttgcac tacctggtgc cattctaaat ttctaagggg aaaaatagaa    8640
agtttgttta ctcttaagat attttatgaa attgtgtgta ctttcctatt ttgccaatta    8700
tgtgcctcaa agattttagt tgagcctag caagaaagta ggaccttcca tttcaatact    8760
tcattaacac ggtgtagtga tactttgtcc cttagactgg tgtttaccag taagatacct    8820
ttaatccact gttaagtatg agtggatttg tttccataga ttagctggat ttccttttgg    8880
tgattgcatt aggtttaaag tacacaggtc tcaactctcc ccaggaaagt ttcccctgtt    8940
tgactccacc tttaaaatcc taagcctgac taggacagcc acaaaccaca caaggtgtaa    9000
aaccatcatc agctaagtgc ccgttttgtt cttgtttacc agaatctcct ttaacttctc    9060
aaagggaagc cgggctttct aatccacgtc aactttattt tagttgtcaa attgggcatt    9120
atattttatg taaattggtc ttttaacatc attttcctga tgaatgttgg tgaccaccac    9180
attgtgaaat ttaagaatcc gtgttgcatg tttggtagct ctctgagttt caggccataa    9240
actcagctcc agaggttacc ttttaagtgc caagaactca agtgcaaggt ggcctactca    9300
aaaatcattt ggtagcattc agttattcat gaattcctct ctcgcatgca ttataaaaag    9360
tgatctgctt taaacaccg taatctgatc ataggcttaa aattaaatat gagtattact    9420
ttcatgtaca aaatatttcc tttatagtct tcatatgccc tttaaaatgc caacaagatt    9480
tcaagtctgt aggcctctag tgaggtgggg tggcaaacca cagctaagtc tcgctcacca    9540
ctgcaagcta agaatggttt ttacatttg ggttggaaaa attttttttg aatatttcat     9600
gacacatgaa aattattcaa atgttagtgc cgataaataa agtggtactg aaacacagcc    9660
acacaaactt gttttttgtac tgtctacagc tactttcaca ctacagccgc agagctgagc   9720
agttcagcag accgtatgtc ccacaatgcc taaaacattg actatgttta cagaaaaagt   9780
ttgctgaccc ctgctctagc aaacgcatcc tttcctactc caccccaatt tgtatttaga    9840
tagtttctct aacagaacgg acaaatgagg ctgcaaacta atttattttt gtcaaaaatc    9900
aatgttttga catccacaga cagtgaaata aagaaatgg cttgctgaaa aacatgagga     9960
gtcctagcca caaatcact gcttaggttg caattgccaa aatgaagcct tcttagaagc    10020
acttctttag tatatacagg tgttggctga agtccgtgcc tcactctggg aaccattctt   10080
agtctccagt gtctcctatt acaaagaagc tggcagaaat aaaaatgaag gggtgagagc   10140
ggttccaccc tagtctcatg gtggaaaatt cattggggag agctgtccag gatatttgga   10200
gtcctgggta gaaggagctt gtaactactt taaagtcgac atctttgcac aggtgattga   10260
gtttctctga cctcattgct tcacctctgt ctcctcccgt ccttccgcac gtgcccacac   10320
acacgcagtt cagccctctt tcctccataa gcctccatcg ttttctcttt tctcctcttg   10380
atcctttcaa gcgagtatct tgttgaattg tatgttctgt tggatctcct ccttcataac   10440
atctggcttg ttggacagaa aaaccctaca gcccaccccc tcccacagcc cacctccact   10500
tttgaaagcc caaattacac ctctcccaga acacagtgtt gacgtaaaata cagttaccca   10560
atattcctgt ttgttcacct atttgctact ttcactcagt agcatcccat tttgtaaaat   10620
gaattccatg gtcaccctgt cacaggaagt aatgaaaaat ccagtgttca gtgtagtggt   10680
gcaaacctga gggcatagag ctgttcatag agggctcttg ttatagccaa acagacacag   10740
caacaatctc accatttata tatatatttt taacttgtcc agctcatcta tggaaaacta  10800
ctcaggtggt atgctgtttg aagcctcatc ttcctacatg aaaattatgg gcatttgtcc   10860
```

-continued

```
caatgatttt gtttcagctg ttctgtaggc tgcataacca ctctgatatt taggtatctg   10920
ctattttatt atcttaaaag acaaattaat ttaattgcat gtgctaggga aaagctacca   10980
tgtacattca ccccaagtaa atagaatcct agatgaatcc tagaaaaata atccctaagc   11040
agataggtag acagaggtaa acattcacat gatttagctc tctagctctt gcactctgaa   11100
cattcttgct ttggttctga cttctgggaa ctgctttgca tttctcctat agatctgtag   11160
ttaagggaac caagggtca ttggggcaaa agcattgttt ctcaaagctc cttgattaag   11220
agaaagaaca gaaatttgca cagaagatag tgtcaaggag tgagaaagtt tgtttgaggg   11280
cagtagctca gtgtggaaga aaatcctgaa gtttctgttg aagccataca atgttctatg   11340
gggttactct ctaagacatt ctctgaggtg tgtgaggaag tcactactcc tagcctttgt   11400
taagatgtaa ttttaaatat tcagttatgg tactatgttt gcaactctcg tcttatcaca   11460
atgcctcagt agtttgttcc cttagaaaca tttagatgtg cacaaattaa tcttttatat   11520
atctaaaggt ttttctatca tgcattggat tgctcagaat aaagtgtctg ttagacttcg   11580
ttttggtaaa taaattctcc ataatgtaga ttaataatat aaaagctttt aatgacacaa   11640
tatatctata tagcctcact gtataattca gaaataaaaa ttgattctgc              11690
```

```
<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
acagcaatat taccagtgac                                                20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
agtttggttt tgatgtcctc                                                20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
agaacccttg cctagaactg                                                20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
```

-continued

```
gactgtggct gtgatgagat                                              20
```

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

```
aaggaagtca tcaacaggag                                              20
```

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

```
caatagccgg acatcctcaa                                              20
```

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
atgatttgga ctgggatgac                                              20
```

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

```
gctctcttgc tgtcactttc                                              20
```

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

```
taagggtct gaaaatagcc                                               20
```

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

```
gatcgcaaaa ctcctacatt                                              20
```

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
cagagcttgg gattcattga                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
taagttcttg gtcacagctg                                              20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
gccagcagag aatgagaata                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
ttttaaagca gccctgatcc                                              20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
ccagcttgta aaattagacc                                              20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
cagattacag cagtggagaa                                              20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
cacgcagagg aaaatagttg                                           20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
accagttgac agaagaatcc                                           20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
atccacattt atccacagag                                           20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
ctttggagga agattctctg                                           20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
agagcctgag cagataaaat                                           20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
tgttcttggg ccatagtgag                                           20

```
<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
gatatcaaga ccaaatggac                                              20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
aatatacggc cgaagaggaa                                              20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
cagatgattg acagacggtt                                              20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
ttctccagac catgcatgtt                                              20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
gagcctggta acatgaatga                                              20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
tcaattagtc tcccttcctg                                              20

<210> SEQ ID NO 31
```

-continued

<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
ctcaccatct gctttcaaac                                              20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
atatcttgct tccctaggtc                                              20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
gtcaccacca tacaggaagt                                              20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
ctcctaccgg caaataaacg                                              20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
ctcactatgg cccaagaaca                                              20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
gtccatttgg tcttgatatc                                              20

<210> SEQ ID NO 37
<211> LENGTH: 20

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
ttcctcttcg gccgtatatt                                                     20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
aaccgtctgt caatcatctg                                                     20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
aaaggtcgtg tcacagcaag                                                     20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
ataaaaggtc gtgtcacagc                                                     20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
atgctctctg gaatgtggat                                                     20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
atgatgctct ctggaatgtg                                                     20

<210> SEQ ID NO 43
<211> LENGTH: 18
<212> TYPE: DNA
```

<213> ORGANISM: Artificial Sequence
<220> FEATURE:
<223> OTHER INFORMATION: Description of Artificial Sequence: Synthetic
      polynucleotide

<400> SEQUENCE: 43
ggcaaaatag gaaagtac                                                   18

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
taaacaccag tctaaggg                                                   18

<210> SEQ ID NO 45
<211> LENGTH: 1455
<212> TYPE: DNA
<213> ORGANISM: Homo sapiens

<400> SEQUENCE: 45
gtcgacatct tgcacaggt gattgagttt ctctgacctc attgcttcac ctctgtctcc       60
tcccgtcctt ccgcacgtgc ccacacacac gcagttcagc cctctttcct ccataagcct     120
ccatcgtttt ctcttttctc ctcttgatcc tttcaagcga gtatcttgtt gaattgtatg     180
ttctgttgga tctcctcctt cataacatct ggcttgttgg acagaaaaac cctacagccc     240 acccctccc acagcccacc tccacttttg aaagcccaaa ttacacctct cccagaacac      300
agtgttgacg taaatacagt tacccaatat tcctgtttgt tcacctattt gctactttca     360
ctcagtagca tcccattttg taaaatgaat tccatggtca ccctgtcaca ggaagtaatg     420
aaaaatccag tgttcagtgt agtggtgcaa acctgagggc atagagctgt tcatagaggg     480
ctcttgttat agccaaacag acacagcaac aatctcacca tttatatata tattttaac     540 ttgtccagct catctatgga aaactactca ggtggtatgc tgtttgaagc ctcatcttcc     600
tacatgaaaa ttatgggcat ttgtcccaat gattttgttt cagctgttct gtaggctgca     660
taaccactct gatatttagg tatctgctat tttattatct taaaagacaa attaatttaa     720
ttgcatgtgc tagggaaaag ctaccatgta cattcaccc aagtaaatag aatcctagat      780
gaatcctaga aaaataatcc ctaagcagat aggtagacag aggtaaacat tcacatgatt     840
tagctctcta gctcttgcac tctgaacatt cttgctttgg ttctgacttc tgggaactgc     900
tttgcatttc tcctatagat ctgtagttaa gggaaccaag gggtcattgg ggcaaaagca     960
ttgtttctca agctccttg attaagagaa agaacagaat ttgcacagaa gatagtgtca     1020
aggagtgaga agtttgttt gagggcagta gctcagtgtg gaagaaaatc ctgaagtttc     1080
tgttgaagcc atacaatgtt ctatggggtt actctctaag acattctctg aggtgtgtga     1140
ggaagtcact actcctagcc tttgttaaga tgtaatttta aatattcagt tatggtacta     1200
tgtttgcaac tctcgtctta tcacaatgcc tcagtagttt gttcccttag aaacatttag     1260
atgtgcacaa attaatcttt tatatatcta aaggttttc tatcatgcat tggattgctc       1320
agaataaagt gtctgttaga cttcgttttg gtaaataaat tctccataat gtagattaat     1380
aatataaaag tctttaatga cacaatatat ctatatagcc tcactgtata attcagaaat     1440
aaaaattgat tctgc                                                    1455

-continued

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
caatagccgg acatcctcaa                                               20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
ttctccagac catgcatgtt                                               20

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
ctgcaccaac aatatccc                                                 18

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
gtagagacag ggtttcac                                                 18

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
ggacagtggt cattggagaa ca                                            22

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
ttagaccgtc cccatagtat cctc                                          24

```
<210> SEQ ID NO 52
<211> LENGTH: 30
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
acatgaaggt catcgagccc tacaggagag                                      30

<210> SEQ ID NO 53
<211> LENGTH: 19
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
gaaggtgaag gtcggagtc                                                  19

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
gaagatggtg atgggatttc                                                 20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
caagcttccc gttctcagcc                                                 20
```